United States Patent
Lamego et al.

(10) Patent No.: US 9,532,722 B2
(45) Date of Patent: Jan. 3, 2017

(54) PATIENT MONITORING SYSTEM

(75) Inventors: Marcelo Lamego, Coto de Caza, CA (US); Massi Joe E. Kiani, Laguna Niguel, CA (US); Ken Lam, Walnut, CA (US); Cristiano Dalvi, Irvine, CA (US); Hung Vo, Garden Grove, CA (US)

(73) Assignee: MASIMO CORPORATION, Irvine, CA (US)

( * ) Notice: Subject to any disclaimer, the term of this patent is extended or adjusted under 35 U.S.C. 154(b) by 519 days.

(21) Appl. No.: 13/527,370

(22) Filed: Jun. 19, 2012

(65) Prior Publication Data

US 2012/0330112 A1    Dec. 27, 2012

Related U.S. Application Data

(60) Provisional application No. 61/499,515, filed on Jun. 21, 2011, provisional application No. 61/645,570, filed on May 10, 2012.

(51) Int. Cl.
*A61B 5/00* (2006.01)
*A61B 5/02* (2006.01)
(Continued)

(52) U.S. Cl.
CPC ....... *A61B 5/02225* (2013.01); *A61B 5/02233* (2013.01); *A61B 5/0002* (2013.01);
(Continued)

(58) Field of Classification Search
CPC ..... A61B 5/0002; A61B 5/0205; A61B 5/222; A61B 5/02233; A61B 17/135; A61B 5/02141; A61B 5/022; A61B 5/0235; A61B 5/021; A61B 5/02225; G06F 19/3406
(Continued)

(56) References Cited

U.S. PATENT DOCUMENTS

| | | |
|---|---|---|
| 2,717,100 A | 9/1955 | Engelder |
| 4,163,290 A | 7/1979 | Sutherlin et al. |

(Continued)

FOREIGN PATENT DOCUMENTS

| | | |
|---|---|---|
| GB | 948 351 A | 1/1964 |
| WO | WO 2013/170095 | 11/2013 |
| WO | WO 2015/020911 | 2/2015 |

OTHER PUBLICATIONS

Advanced / Deluxe One Step Auto-Inflation Blood Pressure monitor model UA-767 Plus. User guide [online]. Life Source, 2009 [retrieved on Apr. 28, 2016]. Retrieved from Internet <URL:https://www.andonline.com/uploads/documents/I-MAN-UA-767PV_0409.pdf>.*

(Continued)

*Primary Examiner* — William Thomson
*Assistant Examiner* — Sebastian X Lukjan
(74) *Attorney, Agent, or Firm* — Knobbe, Martens, Olson & Bear, LLP

(57) ABSTRACT

A patient monitoring system includes an inflatable cuff, a gas reservoir containing a compressed gas, and a sensor. When the inflatable cuff is coupled to a wearer, the gas reservoir supplies gas to the inflatable cuff to inflate the inflatable cuff via gas pathways. As the inflatable cuff inflates, a patient monitor can receive blood pressure data from the sensor and use the blood pressure data to determine the blood pressure of the wearer. The patient monitor can also receive blood pressure data during deflation of the inflatable cuff to determine the blood pressure of the wearer.

28 Claims, 13 Drawing Sheets

(51) Int. Cl.
*A61B 5/022* (2006.01)
*A61B 5/0205* (2006.01)
*A61B 5/021* (2006.01)
*A61B 5/0235* (2006.01)
*G06F 19/00* (2011.01)
*A61B 5/22* (2006.01)
*A61B 17/135* (2006.01)

(52) U.S. Cl.
CPC ............... *A61B 5/021* (2013.01); *A61B 5/022* (2013.01); *A61B 5/0205* (2013.01); *A61B 5/0235* (2013.01); *A61B 5/02141* (2013.01); *A61B 5/222* (2013.01); *A61B 5/725* (2013.01); *A61B 5/7221* (2013.01); *A61B 17/135* (2013.01); *A61B 2560/0214* (2013.01); *G06F 19/3406* (2013.01)

(58) Field of Classification Search
USPC .................... 600/301, 483, 499, 492–493
See application file for complete search history.

(56) References Cited

U.S. PATENT DOCUMENTS

| | | | |
|---|---|---|---|
| 4,305,059 A | 12/1981 | Benton | |
| 4,491,725 A | 1/1985 | Pritchard | |
| 4,800,892 A * | 1/1989 | Perry et al. | 600/490 |
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,163,438 A | 11/1992 | Gordon et al. | |
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,534,851 A | 7/1996 | Russek | |
| 5,561,275 A | 10/1996 | Savage et al. | |
| 5,562,002 A | 10/1996 | Lalin | |
| 5,590,649 A | 1/1997 | Caro et al. | |
| 5,590,696 A | 1/1997 | Phillips et al. | |
| 5,602,924 A | 2/1997 | Durand et al. | |
| 3,316,395 A | 4/1997 | Lavin | |
| 3,316,396 A | 4/1997 | Lavin | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,124,597 A | 9/2000 | Shehada | |
| 6,128,521 A | 10/2000 | Marro et al. | |
| 6,129,675 A | 10/2000 | Jay | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,253,097 B1 | 6/2001 | Aronow et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,301,493 B1 | 10/2001 | Marro et al. | |
| 6,317,627 B1 | 11/2001 | Ennen et al. | |
| 6,321,100 B1 | 11/2001 | Parker | |
| 6,325,761 B1 | 12/2001 | Jay | |
| 6,334,065 B1 | 12/2001 | Al-Ali et al. | |
| 6,336,901 B1 | 1/2002 | Itonaga et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,430,437 B1 | 8/2002 | Marro | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,543,444 B1 * | 4/2003 | Lewis | 128/200.24 |
| 6,565,524 B1 | 5/2003 | Itonaga et al. | |
| 6,580,086 B1 | 6/2003 | Schulz et al. | |
| 6,584,336 B1 | 6/2003 | Ali et al. | |
| 6,595,316 B2 | 7/2003 | Cybulski et al. | |
| 6,597,932 B2 | 7/2003 | Tian et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,639,668 B1 | 10/2003 | Trepagnier | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Kiani et al. | |
| 6,661,161 B1 | 12/2003 | Lanzo et al. | |

(56) References Cited

U.S. PATENT DOCUMENTS

| | | | |
|---|---|---|---|
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,988,992 B2 | 1/2006 | Just et al. |
| 6,993,371 B2 | 1/2006 | Kiani et al. |
| 6,996,427 B2 | 2/2006 | Ali et al. |
| 6,997,878 B2 | 2/2006 | Inagaki et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,153,269 B1 * | 12/2006 | Blansett ................ A61B 5/022 600/490 |
| 7,166,076 B2 * | 1/2007 | Poliac et al. .................. 600/490 |
| 7,186,218 B2 * | 3/2007 | Hersh et al. .................. 600/496 |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,311,670 B2 | 12/2007 | Just et al. |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| 7,678,057 B2 * | 3/2010 | Berkow et al. ................ 600/481 |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |

(56) References Cited

U.S. PATENT DOCUMENTS

| | | |
|---|---|---|
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| 8,547,209 B2 | 10/2013 | Kiani et al. |
| 8,548,548 B2 | 10/2013 | Al-Ali |
| 8,548,550 B2 | 10/2013 | Al-Ali et al. |
| 2003/0125609 A1* | 7/2003 | Becker ................. A61B 5/0002 600/300 |
| 2005/0288597 A1 | 12/2005 | Kishimoto et al. |
| 2006/0211923 A1 | 9/2006 | Al-Ali |
| 2007/0073173 A1* | 3/2007 | Lam et al. ..................... 600/490 |
| 2007/0276263 A1* | 11/2007 | Eide .............. 600/485 |
| 2008/0294455 A1* | 11/2008 | Bharara ............................. 705/2 |
| 2009/0234381 A1 | 9/2009 | Karo |
| 2011/0009757 A1 | 1/2011 | Sano et al. |
| 2011/0092827 A1* | 4/2011 | Hu et al. ...................... 600/485 |
| 2011/0112412 A1 | 5/2011 | Sano et al. |
| 2012/0041276 A1* | 2/2012 | Doreus et al. ................ 600/301 |
| 2012/0059267 A1 | 3/2012 | Lamego |
| 2012/0232416 A1* | 9/2012 | Gilham et al. ................ 600/515 |
| 2012/0240377 A1 | 9/2012 | Ashida |
| 2012/0316449 A1 | 12/2012 | Uesaka et al. |
| 2012/0330169 A1 | 12/2012 | Sano et al. |
| 2013/0060153 A1 | 3/2013 | Kobayashi et al. |
| 2014/0163402 A1 | 6/2014 | Lamego et al. |
| 2015/0038859 A1 | 2/2015 | Dalvi et al. |

OTHER PUBLICATIONS

PCT, International Search Report and Written Opinion, re PCT Application No. PCT/US2013/040438, mailing date Jul. 26, 2013.

Jun Onoderan, Validation of inflationary non-invasive blood pressure monitoring in adult surgical patients, Journal of Anesthesiology, 2011, vol. 25, pp. 127-130.

Osamu Tochikubo, A New Portable Device for Recording 24-h Indirect Blood Pressure in Hypertensive Outpatients, Journal of Hypertension, 1985, vol. 3, pp. 355-357.

International Search Report and Written Opinion re PCT Application No. PCT/US2014/049490, dated Mar. 31, 2015.

Bureau of Indian Standards: "Fire Extinguisher, Carbon Dioxide Type (Portable and Trolley Mounted)—Specification," Aug. 1, 2004, retrieved from the Internet: URL:https://law.resource.org/pub/in/bis/S03/is.2878.2004.html.

International Preliminary Report on Patentability re PCT Application No. PCT/US2014/049490, issued Feb. 9, 2016.

PCT, Inviation to Pay, re PCT Application No. PCT/US2014/049490, mailed Nov. 26, 2014.

* cited by examiner

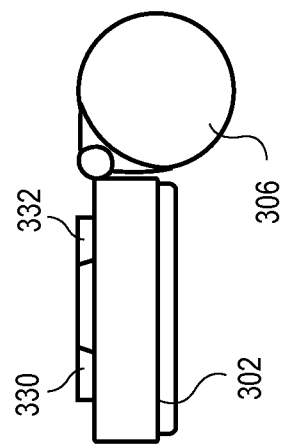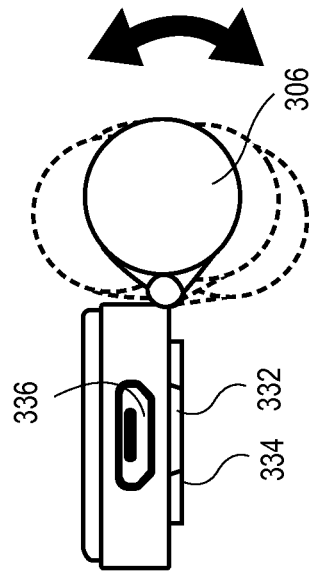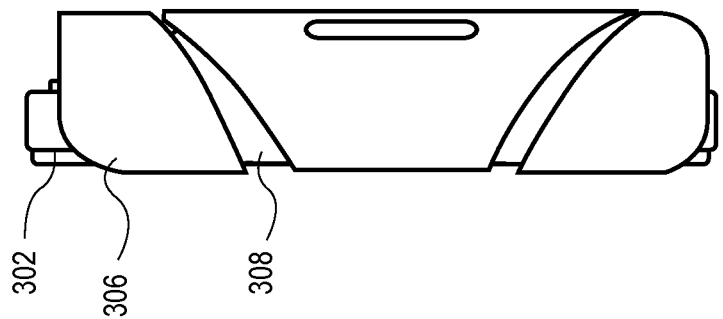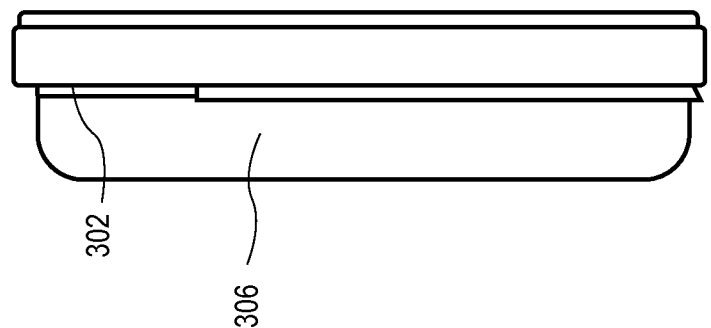

PATIENT MONITORING SYSTEM

RELATED APPLICATIONS

The present application claims the benefit under 35 U.S.C. §119(e) to U.S. Provisional Application Nos. 61/499,515, filed Jun. 21, 2011, entitled "Blood Pressure Monitoring System," and 61/645,570, filed May 10, 2012, entitled "Patient Monitoring System," each of which is hereby incorporated herein in its entirety.

BACKGROUND

Hospitals, nursing homes, and other wearer care facilities typically include patient monitoring devices at one or more bedsides in the facility. Patient monitoring devices generally include sensors, processing equipment, and displays for obtaining and analyzing a medical wearer's physiological parameters such as blood oxygen saturation level, respiratory rate, and the like. Clinicians, including doctors, nurses, and other users, use the physiological parameters obtained from patient monitors to diagnose illnesses and to prescribe treatments. Clinicians also use the physiological parameters to monitor wearers during various clinical situations to determine whether to increase the level of medical care given to wearers. Additionally, monitoring equipment is often used in corporate care facilities, fitness facilities, recreational and home care applications, as well as mobile or other emergency care environments.

Blood pressure (which can refer to diastolic pressure, systolic pressure, and/or some combination or mathematical representation of same) considered one of the principal vital signs, is one example of a physiological parameter that can be monitored. Blood Pressure monitoring is an important indicator of a wearer's cardiovascular status. Many devices allow blood pressure to be measured by manual or digital sphygmomanometer systems that utilize an inflatable cuff applied to a person's arm. The term "sphygmomanoter" is meant to receive its ordinary broad meaning known to an artisan to include devices used to measure blood pressure. These devices often include an inflatable cuff to restrict blood flow and a device capable of measuring the pressure. Other device(s) are used to determine at what pressure blood flow is just starting and at what pressure it is just unimpeded, commonly referred to as "systolic" and "diastolic," respectively. The term "systolic blood pressure" is meant to receive its ordinary broad meaning known to an artisan to include the pressure exerted on the bloodstream by the heart when it contracts, forcing blood from the ventricles of the heart into the pulmonary artery and the aorta. The term "diastolic blood pressure" is meant to receive its ordinary broad meaning known to an artisan to include the pressure in the bloodstream when the heart relaxes and dilates, filling with blood.

In a typical pressure monitoring system, a hand actuated pump or an electric motor inflates the inflatable cuff to a pressure level at or above the expected systolic pressure of the wearer and high enough to occlude an artery. Automated or motorized blood pressure monitoring systems use a motor or pump to inflate the inflatable cuff, while manual blood pressure monitors typically use an inflation bulb. As the air from the inflatable cuff is slowly released, the wearer's blood pressure can be determined by detecting Korotkoff sounds using a stethoscope or other detection device placed over an artery.

Alternatively, digital sphygmomanometers compute diastolic and systolic pressure as the inflatable cuff deflates based on the oscillations observed by a pressure sensor on the cuff. For example, some digital sphygmomanometers calculate the systolic blood pressure as the pressure at which the oscillations become detectable and the diastolic pressure as the pressure at which the oscillations are no longer detectable. Other digital sphygmomanometers calculate the mean arterial pressure first (the pressure on the cuff at which the oscillations have the maximum amplitude). The diastolic and systolic pressures are then calculated based on their fractional relationship with the mean arterial pressure. Other algorithms are used, such as identifying the change in slope of the amplitude of the pressure fluctuations to calculate the diastolic pressure.

As mentioned above, the foregoing methods of determining blood pressure include inflating the cuff to a pressure high enough to occlude an artery and then determining blood pressure during deflation of the inflatable cuff. Occluding the artery and then determining blood pressure during deflation can have a number of drawbacks. For example, inflating the inflatable cuff to a pressure higher than systolic pressure can cause pain and discomfort to the wearer. Other adverse effects can include limb edema, venous stasis, peripheral neuropathy, etc, or simply wearer interruption. In addition, as the artery is completely occluded prior to each measurement, sufficient time must elapse between measurements to ensure accurate results. Furthermore, manual systems make it difficult to measure blood pressure during inflation of the inflatable cuff due to the difficult of inflating the inflatable cuff at an approximately constant rate using an inflation bulb.

Digital blood pressure monitors can have additional drawbacks. The motors used to pump gas into the cuff are often noisy and can disturb wearers at rest. This is especially problematic in recovery situations. In addition to auditory noise in automated or motorized systems, the motors can cause electrical noise in sensor signals making signal processing used to identify reference points for blood pressure detection unreliable and difficult. Furthermore, portable motorized blood pressure monitors require a significant amount of power to produce the air pressure required to inflate the cuff. Since batteries are often used to provide power, designers often use large batteries and/or batteries that frequently need to be recharged or replaced. When a large batter is chosen, its size often offsets the goals of portability as an appropriate housing becomes more cumbersome and less convenient.

SUMMARY

Based on at least the foregoing drawbacks, a need exists for a patient monitoring system that relatively quickly determines blood pressure measurements without necessarily greatly disturbing a patient. Moreover, a need exists for a portable patient monitoring system with battery longevity. Accordingly, the present disclosure includes embodiments of a patient monitoring system including a gas reservoir filled with a sufficient quantity of compressed gas to inflate an inflatable cuff and a sensor to detect blood pressure data. The gas in the gas reservoir can inflate the inflatable cuff at a controlled rate, such as, for example, at an approximately constant rate. Manual and/or electronically controlled regulators and/or valves can be used to control the flow rate of the gas into and out of the inflatable cuff. In some embodiments, the regulators and/or valves can be electronically controlled using pulse-width modulation (PWM) schemes.

A patient monitor can also be included as part of the patient monitoring system. During inflation or deflation of the inflatable cuff, the patient monitor can receive the blood pressure data from the sensor and use the blood pressure data to determine output measurements responsive to the blood pressure of the wearer. The sensor can be a pressure sensor and can be used to detect pressure variations in the inflatable cuff due to inflation, deflation, and blood flow in an artery of the wearer. Alternatively, the sensor can be an auditory sensor or stethoscope. A caregiver can use the stethoscope or auditory sensor to determine blood pressure measurements without the use of the patient monitor.

For purposes of summarizing the invention, certain aspects, advantages and novel features of the invention have been described herein. Of course, it is to be understood that not necessarily all such aspects, advantages or features will be embodied in any particular embodiment of the invention.

BRIEF DESCRIPTION OF THE DRAWINGS

Various embodiments will be described hereinafter with reference to the accompanying drawings. These embodiments are illustrated and described by example only, and are not intended to limit the scope of the disclosure. In the drawings, similar elements have similar reference numerals.

FIGS. 3A-3G illustrate an exemplary embodiment of a patient monitoring system configured to be worn by a user;

DETAILED DESCRIPTION

Figure 1A:
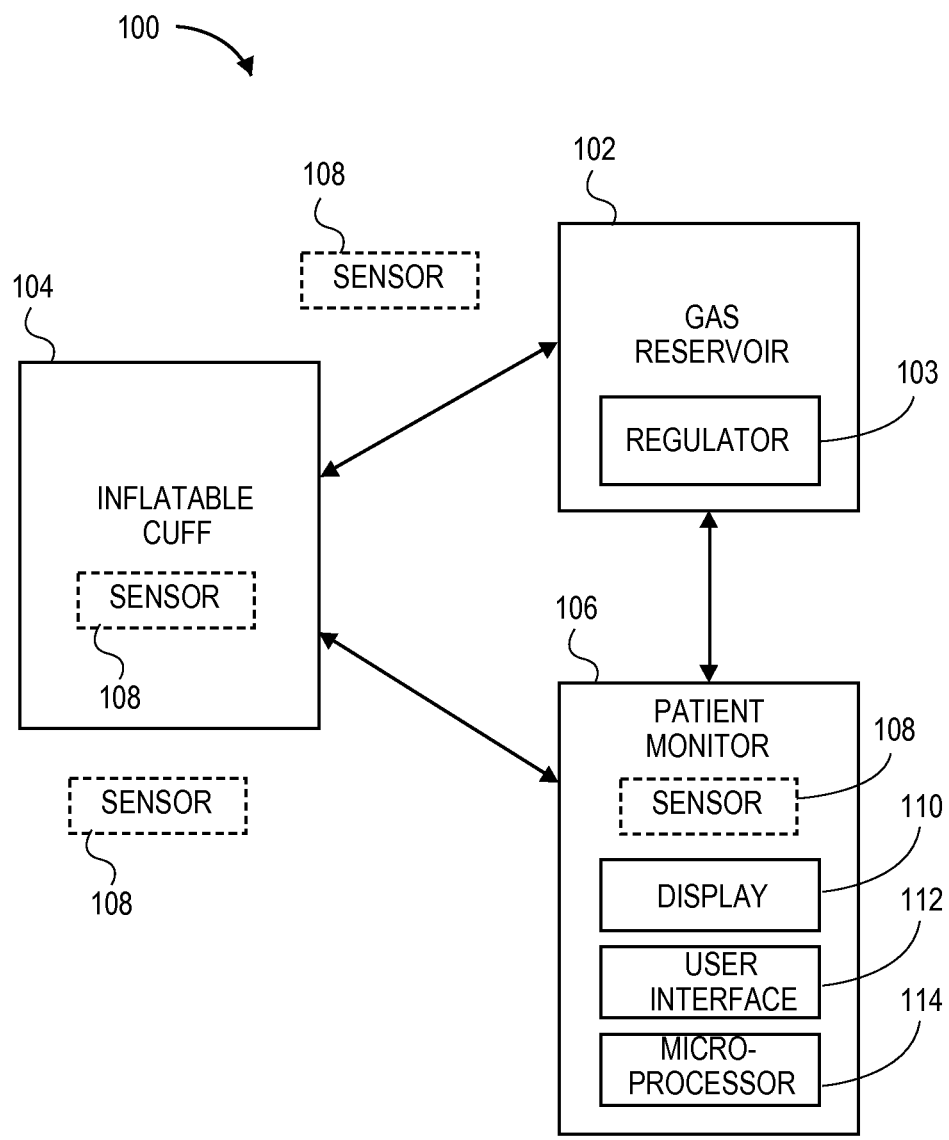
FIG. 1A is an exemplary block diagram illustrating an embodiment of a patient monitoring system.

A patient monitoring system advantageously includes a gas reservoir filled with sufficient quantities of compressed gas to inflate an inflatable cuff. The gas reservoir provides several advantages to the blood pressuring monitoring system, including portability, reusability, disposability, reduction in auditory noise and electrical noise, and the ability to measure blood pressure during inflation of the blood pressure cuff.

In an embodiment, the gas reservoir of the patient monitoring system inflates the inflatable cuff at an approximately constant rate with less auditory noise. By providing a quieter environment, the patient monitoring system is capable of taking blood pressure measurements without significantly disturbing the wearer. In addition, the use of the gas reservoir can significantly reduce the amount of potentially interfering electrical noise on electrical signals from one or more sensors. Furthermore, the addition of the gas reservoir allows the patient monitor to take blood pressure measurements during inflation of the inflatable cuff.

Measuring blood pressure during inflation can reduce the time required for blood pressure measurements and the amount of pressure used. In some embodiments, the patient monitoring system can measure blood pressure in 15-20 seconds or less. Furthermore, measuring blood pressure during inflation can reduce or eliminate the need to occlude a wearer's artery.

In addition, the gas reservoir of the present disclosure can be manufactured as a smaller portable patient monitor. The gas reservoir can eliminate the need for a pump and/or motor in the portable patient monitor, thereby reducing its size. In an embodiment, the gas in the gas reservoir can be used to generate electricity for the portable patient monitor, thereby reducing or eliminating the need for a battery and further reducing the size of the portable patient monitor.

In addition to the foregoing, other embodiments of the present disclosure include patient monitoring systems with canister inflation and one or more backup inflation systems. For example, in an embodiment, when the patient monitor is for whatever reason without sufficient gas to make a reliable, accurate blood pressure measurement, a motor and pump and/or inflation bulb may advantageously be used in place of the canister. In an embodiment, the foregoing backup inflation system(s) is part of the patient monitoring system and is activated when gas from the gas canister is unavailable, unwanted, insufficient, or the like. For example, in an embodiment, a user may designate which inflation system they would prefer based on, for example, proximity to power, battery use desires, gas use management, portability, emergency, surgical, other critical monitoring environments, or the like. In still further additional embodiments, the forgoing backup inflation system(s) are separate systems that connect to the monitor in place of the canister.

In an embodiment, measurements by a patient monitoring system of the present disclosure may be controlled through applications or software executing on one or more computing devices, such as a smart phone, tablet computer, portable digital devices of all types, or other computing devices or systems or combinations of the same. In an embodiment, the computing device may include modules governing the measurement frequency during periodic measurements. In an embodiment, the applications or software may include exercise related software configured to use blood pressure measurements to enhance feedback to users on a performance of the exercise, such as, for example, calories spent, heart rate trending or the like. Additionally, inputs may include type of exercise, user demographics like height, sex, age, weight or the like. Based on the inputs, the portable digital device can provide exercise recommendations, such as walking, running, cycling or other physical activities.

In still additional embodiments of the disclosure, the patient monitoring system may communicate with electronics of the canister for quality control to ensure it is an authorized canister, for canister characteristics information, such as type, pressure, size, manufacturer, or the like. Simultaneously, the monitor may communicate with electronics of the cuff and or sensors.

In additional embodiments of the disclosure, a patient monitoring system may connect to a gas supply supplied at a premises. For example, a hospital or other caregiver environment may have pressurized gas available from connection in a room, group of rooms, beds, instruments, or the like and straightforward connection of the monitor to the gas supply may supplement or replace the canister.

In yet another embodiment, a display of a patient monitoring system may present measurement data in a manner that reduces a need for translation when used by speakers of different languages. For example, the display may include icons, numbers, colors, analog style digital gauge icons, such as a dial, gas bar or the like, audible and/or visual alarms, combinations of the same or the like to convey measurement information to a user or caregiver.

In still further embodiments, the monitor may be entirely portable and configured to mount to an arm, wrist, waist or belt harness, carried in a pocket of the like.

Various embodiments will be described hereinafter with reference to the accompanying drawings. These embodiments are illustrated and described by example only, and are not intended to be limiting.

FIG. 1 is a block diagram illustrating an embodiment of a patient monitoring system 100 for measuring blood pressure of a wearer, which may also be referred to as taking blood pressure measurements, using an inflatable cuff 104. The patient monitoring system 100 can be used to measure the blood pressure of a wearer during inflation, deflation or both. In an embodiment, the patient monitoring system 100 includes a gas reservoir 102, the inflatable cuff 104 and a patient monitor 106.

The gas reservoir 102 houses compressed gas and is operatively connected to the inflatable cuff 104 via a gas pathway. In an embodiment, a regulator 103 is in the gas pathway between the inflatable cuff 104 and reservoir 102. In an embodiment, the regulator 103 provides a desired pressure or flow in the cuff-side so long as there is sufficient pressure on the reservoir side. Thus, gas flows from the gas reservoir 102, through the regulator 103 to the bladder of the inflatable cuff 104. In one embodiment, the gas pathway is an airtight pathway constructed of any number of materials including, but not limited to, metal, plastic, cloth, combinations of the same or some other airtight material.

The gas reservoir 102 can be implemented using one or more disposable or reusable gas tanks, cylinders, bottles, canisters, or cartridges, of any number of shapes or sizes, and can be located in the same room as the wearer, or can be remotely located from the wearer, such as in a different room or even in a different building. For example, the gas reservoir 102 can include a large gas tank that remains in a stationary location. The gas reservoir 102 can be large enough to contain sufficient gas for a large number of blood pressure readings (e.g. more than 100). Furthermore, the gas reservoir 102 can store compressed gas at any number of PSI levels. For example, the gas reservoir can store compressed gas up to about 6000 PSI or more, depending on the safety conditions of the environment. Furthermore, the gas tank can be configured to supply gas to multiple inflatable cuffs 104, thereby limiting the number of gas tanks used for multiple wearers. When the pressure levels in the gas tank reach a threshold, the gas tank can either be refilled, replaced or a combination of both. For example a rotating cache of gas tanks can be used as the gas reservoir 102.

Alternatively, the gas reservoir 102 can be implemented using a small gas tank of any number of sizes. For example, the gas reservoir 102 can be implemented using a gas tank that is small enough to fit in the palm of a hand, such as a carbon dioxide ($CO_2$) cartridges similar to or the same as those used for paint ball guns, tire inflation, or the like. $CO_2$ cartridges are available from a number of different manufacturers and distributors, such as the AirSource 88 Gram Pre-filled Disposable $CO_2$ cartridge available from Crosman (Product Code: CRO-88-GRAM). The PSI levels for smaller gas tanks can also differ greatly and can store compressed gas up to about 2000 PSI or more. In one embodiment, the gas reservoir 102 is implemented using a gas tank of compressed gas at about 1000 PSI. The small gas reservoir 102 can be used where mobility is desired. For example, paramedics or first responders can carry a small gas reservoir 102 for measuring blood pressure of persons needing emergency medical care. Using the gas reservoir 102, the emergency personnel (or some other user) can measure the blood pressure of the wearer during inflation of the inflatable cuff, deflation, or a combination of the two. The measurements can be taken using a patient monitor 106, manually using a stethoscope, or other methods.

In one embodiment, a pressure regulator, or regulator 103, placed at an opening of the gas reservoir 102 controls whether gas can exit the gas reservoir and the amount of gas allowed to exit. In one embodiment, the regulator 103 is a valve. The regulator 103 can also be configured to control the rate at which gas flows to the inflatable cuff 104, as well as the pressure of the gas or PSI level. The regulator 103 can include a second regulator near the opening of the gas reservoir 102 or in the gas pathway to form a two-stage pressure regulator. Additional regulators can be added as desired. The regulator 103 and/or valve can be implemented using any number of different valves, such as a globe valve, butterfly valve, poppet valve, needle valve, etc., or any other type of valve capable of operating as a variable restriction to the gas flow. Furthermore, the regulator 103 can include a pressure gauge to identify the pressure levels of the gas exiting the gas reservoir 102 and/or in the gas pathway.

Using the regulator 103, the inflatable cuff 104 can be inflated at a controlled rate, such as, for example, an approximately constant rate or linear rate. By inflating the inflatable cuff at a controlled rate, the wearer's blood pressure can be measured during inflation and without occluding the artery. The regulator 103 can further include a wireless transmitter for communication with the patient monitor 106, which in turn may electronically control and/or monitor the flow of gas through the regulator 103. Alternatively, the regulator 103 can communicate with the patient monitor via wired communication. Additionally, the gas reservoir 102 can include a pressure gauge to monitor the remaining pressure and/or the amount of compressed gas remaining in the gas reservoir 102. The pressure gauge can communicate the pressure levels to the patient monitor 106 via wired or wireless communication, similar to the regulator 103. Once the pressure gauge indicates a threshold pressure level or gas level has been reached, the patient monitor 106 can indicate that the gas reservoir 102 should be replaced or refilled.

The gas reservoir 102 can contain any number of compressed gases to inflate the inflatable cuff 104. For example, the gas reservoir 102 can contain compressed air, carbon dioxide, nitrogen, oxygen, helium, hydrogen, etc. Any number of other gases can be used to inflate the inflatable cuff 104. Furthermore, the gas reservoir 102 may house enough gas to inflate the inflatable cuff 104 without the use of a motor or pump during the inflation. The gas reservoir 102 can be pre-filled with gas near the wearer or at a remote site away from the wearer. In one embodiment, the gas reservoir 102 is filled with gas prior to being associated with the inflatable cuff 104. Pre-filling the gas reservoir 102 prior to use can significantly reduce the ambient noise caused during inflation of the inflatable cuff 104. In addition, by using the gas reservoir 102, the electrical noise from a motor can be removed. The reduction in ambient and electrical noise and the approximately constant rate of inflation of the inflatable cuff 104 allows the patient monitor 106 to measure the wearer's blood pressure while the inflatable cuff 104 is inflating. In addition, the gas reservoir 102 can be used to quickly inflate the inflatable cuff 104 for blood pressure measurements taken during deflation of the inflatable cuff 104.

In some embodiments, multiple gas reservoirs 102 are included as part of the patient monitoring system 100. The multiple gas reservoirs 102 can be used for backup purposes or for different tasks. For example, a first gas reservoir 102 can be a large gas reservoir and can be used to supply gas to the inflatable cuff 104 when the user is stationary. A second optionally smaller gas reservoir 102 can also be provided. When the user moves away from the first gas reservoir 102, the first gas reservoir can be disconnected from the inflatable cuff 104 and the second gas reservoir 102 will supply the gas to the inflatable cuff 104. In certain embodiments, a pump may be connected to the inflatable cuff 104 and used when the user is stationary. When the user moves, the pump is disconnected and the gas reservoir 102 supplies the gas to the inflatable cuff 104.

In some embodiments the gas reservoir 102 includes an identifier that identifies the gas reservoir 102 to the patient monitor 106. The identifier can be implemented using one or more memory chips or RFIDS located on the gas reservoir and/or one or more circuit elements, such as resistors, capacitors, inductors, op-amps, etc. The identifier can include additional information regarding the gas reservoir 102, such as the type of gas reservoir, manufacturing date and/or location, storage capacity or amount of gas that the gas reservoir 102 can hold, the quantity of gas in the gas reservoir, PSI levels, usage data, expiration dates, product histories, etc.

The patient monitor 106 can use the identifier to determine whether to use the gas reservoir 102, whether the gas reservoir 102 is compatible with the patient monitor 106, or whether the reservoir 102 is from an authorized supplier. The identifier can be unique for each gas reservoir 106 or for a set of gas reservoirs 102. In some embodiments, the identifier indicates that the gas reservoir can be used with the patient monitor 106. In certain embodiments, only gas reservoirs 102 with a particular identifier are used with the patient monitor 106. Accordingly, gas reservoirs 102 that do not include the particular identifier can be rejected and/or ignored by the patient monitor 106. In an embodiment, an emergency use override may allow for measurements, or a specific number of measurements in an emergency situation, even when, for example, the identifier does not indicate an authorized supplier but is otherwise safe for use.

It is to be understood that other techniques exist for implementing the gas reservoir 102 without departing from the spirit and scope of the description. For example, the gas reservoir 102 can be implemented using the central gas line of a building, such as a hospital or other healthcare facility. Alternatively, the gas reservoir 102 can be implemented using a bulb, bladder, pump, or the like. In still further embodiments, the foregoing alternatives may serve as backup options if the reservoir 102 is empty or otherwise not functional.

The inflatable cuff 104 includes a bladder and fills with gas in a manner controlled by the patient monitor 106 or manually, and is used to at least partially obstruct the flow of blood through a wearer's artery in order to measure the wearer's blood pressure. The inflatable cuff 104 can be attached to a wearer's arm or other location, and can be inflated automatically (e.g., via intelligent cuff inflation) or manually to obtain blood pressure data. Blood pressure data can include any type of signal received from a sensor sufficiently responsive to blood pressure to provide an indicator thereof to a user. Blood pressure data can be in the form of pressure sensor data, auditory sensor data, and the like.

The inflatable cuff 104 can further include a wireless transmitter for wireless communication with the patient monitor 106. Alternatively, the inflatable cuff can include cables for sending and receiving information to and from the patient monitor 106. The inflatable cuff can receive gas from a gas reservoir 102 via a gas pathway. Furthermore, the inflatable cuff can include a release valve for releasing the gas stored in the inflatable cuff once inflated. The release valve can be actuated electronically by the patient monitor 106 or manually by a user. In some embodiments, the release valve can be used when the pressure in the inflatable cuff 104 reaches unsafe levels or when the inflatable cuff 104 has been inflated beyond a threshold period of time. In certain embodiments, the release valve can be actuated electronically using PWM signals. In some embodiments, the inflatable cuff 104 is a disposable cuff that can be discarded after a one or a few uses. In certain embodiments, the inflatable cuff 104 can be reused many times and cleaned or sterilized between uses.

A sensor 108 can be placed in close proximity to the inflatable cuff 104 to monitor the inflatable cuff 104 during inflation and deflation. Alternatively, the sensor 108 can be located in the patient monitor 106 along a gas pathway between the gas reservoir 102 and inflatable cuff 104, or at some other location where it is able to collect sufficient data for the patient monitor 106 to determine the blood pressure of the wearer.

The sensor 108 can be a pressure sensor or an auditory sensor. In one embodiment, the sensor 108 communicates signals responsive to the pressure in the inflatable cuff 104 to the patient monitor 106 via wired or wireless communication. The patient monitor uses the signal to determine a blood pressure measurement or change in blood pressure of the wearer. The patient monitor 106 can additionally use the pressure measurements to determine if the pressure in the inflatable cuff 104 is above a threshold or is at an unsafe level. If the pressure in the inflatable cuff 104 is above a threshold or is at an unsafe level, the patient monitor 106 can actuate an emergency release valve to deflate the inflatable cuff 104. In an embodiment where the sensor 108 is an auditory sensor, the sensor 108 can be used to detect Korotkoff sounds. In one embodiment, the sensor 108 comprises a stethoscope.

In an embodiment, the patient monitor 106 includes a display device 110, a user interface 112, and a microprocessor or microcontroller or combination thereof 114. The patient monitor 106 can further include a number of components implemented by the microprocessor 114 for filtering the blood pressure data received from the sensor 108 and determining the blood pressure of the wearer. The patient monitor 106 can be a dedicated device for determining blood pressure and other physiological parameters, a portable electronic device configured to execute a program or application that determines blood pressure and other physiological parameters, or can be part of a larger patient monitoring device, such as those devices described in U.S. patent application Ser. No. 09/516,110, titled "Universal/Upgrading Pulse Oximeter," filed Mar. 1, 2000; U.S. patent application Ser. No. 12/534,827, titled "Multi-Stream Data Collection System For Noninvasive Measurement Of Blood Constituents," filed Aug. 3, 2009; U.S. patent application Ser. No. 12/497,523, titled "Contoured Protrusion For Improving Spectroscopic Measurement Of Blood Constituents," filed Jul. 2, 2009; U.S. patent application Ser. No.

12/882,111, titled "Spot Check Monitor Credit System," filed Sep. 14, 2010; U.S. patent application Ser. No. 13/308,461, titled "Handheld Processing Device Including Medical Applications For Minimally And Non Invasive Glucose Measurements," filed Nov. 30, 2011 and U.S. patent application Ser. No. 11/366,995, titled "Multiple Wavelength Sensor Equalization," filed Mar. 1, 2006. Each of which is incorporated by reference herein.

In some embodiments, the patient monitor 106 is configured to communicate with the inflatable cuff 104 and/or the gas reservoir 102 via wired or wireless communication, such as LAN, WAN, Wi-Fi, infra-red, Bluetooth, radio wave, cellular, or the like, using any number of communication protocols. The patient monitor 106 can further be configured to determine blood pressure measurements of a wearer when the inflatable cuff 104 is being inflated with gas from the gas reservoir 102, during deflation of the inflatable cuff 104, or a combination of both. The patient monitor 106 can use the microprocessor 114, the filtering component, and blood pressure monitoring component to determine the blood pressure measurements. The blood pressure measurements determined by the patient monitor 106 can be displayed on the display 110. In addition, the display 110 can display blood pressure data and filtered blood pressure data in the form of plots of the pressure of the inflatable cuff and plots of the pressure oscillations in the inflatable cuff 104 caused by blood flowing through an artery of the wearer. Furthermore, the patient monitor 102 can calculate and the display 110 can display additional physiological parameters, such as heart rate, perfusion, oxygen saturation, respiration rate, activity information, temperature, and the like, combinations thereof or the trend of any of the above.

The user interface 112 can be used to allow a user to operate the patient monitor 106 and obtain the blood pressure measurements and/or other physiological parameters. Furthermore, the user interface 112 can allow a user to set or change any number of configuration parameters. For example, using the user interface 112, a user can determine what is displayed on the display 110, such as the blood pressure measurements during inflation and/or deflation, additional physiological parameters, the pressure plots, and/or other physiological parameters, etc. Furthermore, the user interface 112 can allow a user to set what measurements of what parameters the patient monitor 106 should take. For example, the user can set the configuration parameters to take blood pressure measurements only during inflation or deflation. Alternatively, the user can use the user interface 112 to set the configuration parameters to take blood pressure measurements during inflation and deflation and then use both measurements to determine an appropriate blood pressure. In addition, using the user interface 112, the user can determine how often the patient monitor 106 takes blood pressure measurements, or other physiological parameter measurements. The user interface 112 can further be used for any other type of configuration parameters that can be set or changed by a user. In some embodiments, the user interface 112 is implemented as an application of a portable electronic device.

In some embodiments, the patient monitor 106 monitors the use of the gas reservoir. To monitor the use of the gas reservoir 102, the patient monitor can monitor the number of times that the gas reservoir 102 is used to fill the inflatable cuff 104, the amount of time that the gas reservoir 102 is supplying gas, current pressure levels within the gas reservoir 102, and the like.

The patient monitor 106 can store usage data of the gas reservoir 102 in a memory device located on or in the gas reservoir 102. In some embodiments, the memory device is the identifier discussed previously. In certain embodiments, the memory device is located in the patient monitor 106 or some other location, and a unique identifier of the gas reservoir 102 can be used to correlate a particular gas reservoir 102 with its usage data.

Each time the gas reservoir 102 is used to inflate the inflatable cuff 104, the patient monitor 106 can update the usage data. In some embodiments, the usage data reflects a total number of instances in which the gas reservoir has been used to inflate the cuff 104. In certain embodiments, the usage data reflects the amount of time that the gas reservoir 102 has been supplying gas and the rate at which the gas has been supplied. Further embodiments can use any combination of the embodiments described herein.

Using the number of times that the gas reservoir has been used to fill the inflatable cuff 104 and other data regarding the gas reservoir 102, the patient monitor 106 can determine when the gas reservoir 102 will run out of gas and/or the number of remaining uses. In certain embodiments, the patient monitor 106 uses the storage capacity of the gas reservoir 102 and the amount of gas used to fill the inflatable cuff 104 to determine the number of times the gas reservoir can be used to fill the inflatable cuff 104 before it should be replaced. In some embodiments, the patient monitor 106 calculates the total amount of time the gas reservoir 102 is able to output gas before it should be replaced based on the storage capacity and the rate of flow of the gas. The patient monitor 106 can also account for any change to the rate of flow. Additional methods can be used to calculate whether the gas reservoir 102 should be replaced. For example, a pressure sensor can be used to determine the pressure levels within the gas reservoir 102.

When the usage data indicates that the capacity of the gas reservoir 102 is about to be (or has been) met, the patient monitor 106 can alert a user that the gas reservoir 102 should be replaced. The patient monitor 106 can alert a user by sounding an alarm, flashing a light, sending an email, text message, fax, page, or the like to a user.

In an embodiment where many canisters may be in circulation with one or more monitors, the monitor may use a canister ID to track usages for different canisters, such as, for example, the identifier. In embodiments where each canister includes accessible memory storage, the usage information stored in such memory may be updated by the monitor or canister during use.

Figure 1B:
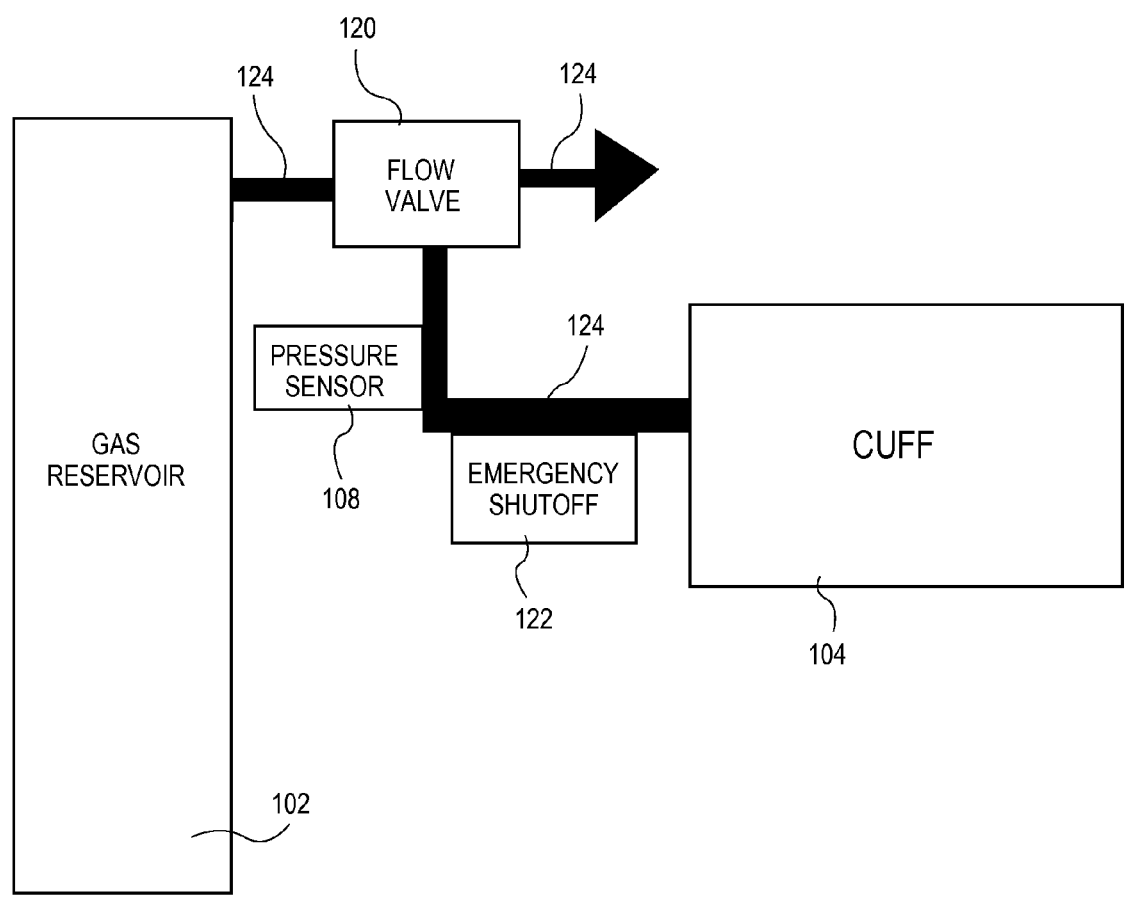
FIG. 1B is an exemplary block diagram illustrating an embodiment of gas pathways between different components of the patient monitoring system of FIG. 1A.

FIG. 1B illustrates a block diagram of gas pathways between different components of the patient monitoring system 100. As described previously, the patient monitoring system 100 can include a gas reservoir 102, an inflatable cuff 104, a patient monitor (not shown), a pressure sensor 108, a flow valve 120, an emergency shutoff 122, and gas pathways 124. The gas from the gas reservoir 102 travels via the gas pathways 124 and valve 120 to the inflatable cuff 104.

The flow valve 120 can direct the gas from the gas reservoir 102 to the cuff 104 or to an exit pathway. During deflation of the cuff 104, the flow valve can direct the gas from the cuff 104 to the exit pathway. In some embodiments, the flow valve is controlled using PWM signals. The pressure sensor 108 measures the pressure within the gas pathway as well as the changes in pressure due to the blood pressure of the wearer. The emergency shutoff 122 can be used to quickly deflate the cuff 104 as desired. The components illustrated in FIG. 1B can be located in different positions. For example, the pressure sensor 108 and emergency shutoff 122 can be located on or in the cuff 104.

Figure 2:
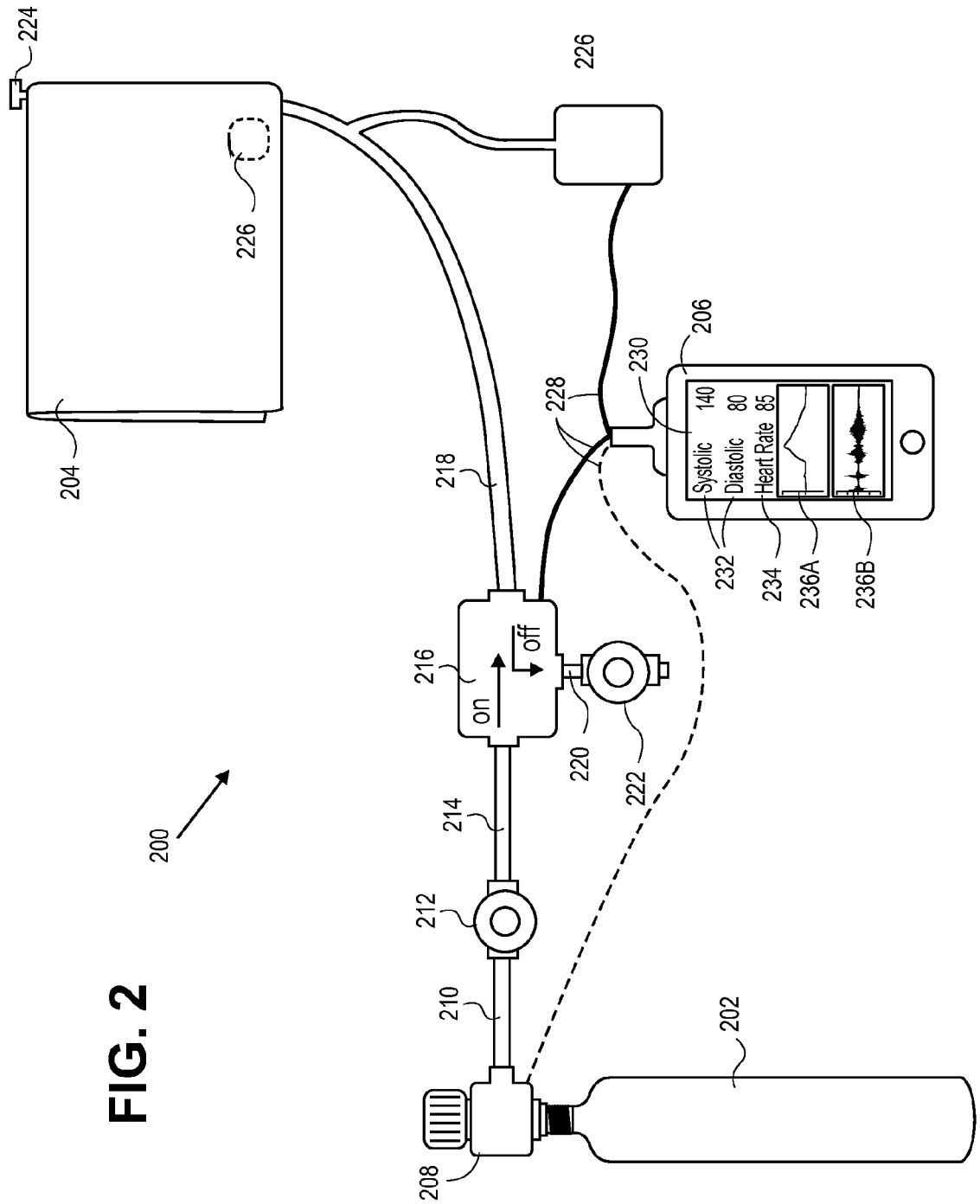
FIG. 2 is an exemplary system diagram illustrating an embodiment of the patient monitoring system of FIG. 1.

FIG. 2 illustrates a patient monitoring system 200 similar to the patient monitoring system 100 of FIG. 1. Similar to the patient monitoring system 100 of FIG. 1, the patient monitoring system 200 of FIG. 2 includes a gas reservoir 202, an inflatable cuff 204, a patient monitor 206, and a sensor 226 a like gas pathway between the reservoir 202 and cuff 204. In addition, the patient monitoring system 200 includes the gas pathway having a number of gas pathway segments 210, 214, 218 and valves 212, 216, 222 facilitating the movement of gas throughout the system. The gas reservoir 202, the inflatable cuff 204, the patient monitor 206, the valve 216, and the sensor 226 can communicate using wired or wireless communication. Cables 228 can be used to facilitate communication between the various components of the patient monitoring system 200. The various components can be connected to each other or connected to a central location, such as the patient monitor 206. Alternatively, the cables 228 can be removed and the patient monitor 202 can communicate with the other components of the patient monitoring system via wireless communication.

As mentioned previously with reference to FIG. 1, the gas reservoir 202 can be implemented using one or more gas tanks of any number of different sizes. In addition, the gas reservoir 202 can be located in the same room as the wearer or can be located at a remote location, such as in a different room or different building from the wearer. In such an embodiment, the gas pathway runs from the wearer to the remote location where the gas reservoir 202 is located. In addition, the gas reservoir 202 can be filled with any number of different gases prior to use with the wearer 218. In other words, the gas reservoir 202 can be filled with gas prior to installation with the other components of the patient monitoring system 200. In one embodiment, the gas reservoir 202 is filled with a compressed gas.

Furthermore, in an embodiment, the gas from the gas reservoir 202 can be used to generate electricity for the patient monitoring system 200. A small turbine can be located near the opening of the gas reservoir 202, along the gas pathway, or near an opening of the inflatable cuff 204. As the gas flows by the turbine and into the inflatable cuff 202, the turbine rotates. The rotation of the turbine can be used to generate electricity for the patient monitoring system 200. The electricity can be fed to the patient monitor 206 so that the patient monitor 206 can process received signals and determine output measurements for the blood pressure of the wearer as the inflatable cuff inflates. Another turbine can be located near the release valve 224 of the inflatable cuff 204 or the gas pathway segment 220. When the release valve 224 of the inflatable cuff 204 is opened or the valve 216 is actuated, the exiting gas causes the turbine to rotate, thereby generating electricity. The generated electricity can be fed to the patient monitor 206, allowing the patient monitor to process received signals and determine output measurements for the blood pressure of the wearer as the inflatable cuff 204 deflates.

Using the gas reservoir 202 to inflate the inflatable cuff 204 can significantly reduce the ambient noise caused by the patient monitoring system, resulting in a quieter environment for the wearer. In addition, the gas reservoir 202 can supply gas at an approximately constant pressure and rate. Thus, the patient monitoring system 200 can inflate the inflatable cuff at an approximately constant rate without the auditory and electrical interfering noise of a motor or pump, resulting in a cleaner signal for the patient monitor 206. Furthermore, by using the gas reservoir 202, the patient monitor can measure the wearer's blood pressure during inflation of the inflatable cuff 204.

By measuring the blood pressure during inflation of the inflatable cuff, the patient monitoring system 200 can measure the blood pressure in less time and using less pressure. Furthermore, measuring blood pressure during inflation of the inflatable cuff can reduce, and in some embodiments completely remove, the amount of time that the artery is occluded, allowing for more frequent blood pressure readings and reduced discomfort for the patient.

The gas reservoir 202 is operatively connected with the inflatable cuff 204 via the regulator 208, gas pathway segments 210, 214, 218 and valves 212, 216. The gas pathway and gas pathway segments 210, 214, 218 can be made of any air-tight material, such as a plastic tube, metal, cloth, combinations or the like. Gas from the gas reservoir 202 flows through the gas pathway segments 210, 214, 218 to inflate the inflatable cuff 204. In an embodiment, the regulator 208, the gas pathway segments 210, 214, 218 and the valves 212, 216, 222 control the direction and rate of gas flow throughout the patient monitoring system 200. The regulator 208, which can also be a valve, located near the opening of the gas reservoir 202 controls the pressure of the gas exiting the gas reservoir 202 and along the gas pathway segment 210. The valve 212 controls the pressure of the gas exiting gas pathway segment 210 and along gas pathway segments 214, 218 to the inflatable cuff 204. The regulator 208 and valve 212 can be configured as a two-stage pressure regulator and used to maintain an approximately constant pressure of gas entering the inflatable cuff 204. The approximately constant pressure of gas may advantageously lead to an approximately constant rate of inflation of the inflatable cuff 204. The regulator 208 and valve 212 can be configured to maintain any number of pressure levels in the gas pathway segments 210, 214, 218. In one embodiment, the regulator 208 and valve 212 are configured to maintain a pressure of approximately 6 PSI (pounds per square inch) along the gas pathway segment 214 and gas pathway segment 218.

The valve 216 located along the gas pathway segments 210, 214, 218 can be used to control the direction of the gas flow throughout the patient monitoring system 200. In an "on" configuration, the valve 216 allows the gas to pass from the gas pathway segment 214 to the gas pathway segment 218 into the inflatable cuff 204. In an "off" configuration, the valve 216 closes the gas pathway between the gas reservoir 202 and the inflatable cuff 204 and opens a gas pathway from the inflatable cuff 204 and gas pathway segment 218 to the gas pathway segment 220 and through valve 222. The valve 216 can be actuated electronically using the patient monitor 206 or manually by a user. For safety, the default position for the valve 216 can be the "off" configuration. In this way, should there be any malfunctions, the inflatable cuff 204 can deflate. In an embodiment, the valve 216 is a three-way valve. The valve 216 can be implemented in a number of different ways without departing from the spirit and scope of the description.

The valve 222 is similar in most respects to the valve 212 and can control the rate at which gas is allowed to exit the inflatable cuff 204. The valves 212, 222 can be implemented as any number of different valves, such as globe valve, butterfly valves, poppet valves, needle valves, proportional valves, etc., or any other type of valve capable of operating as a variable restriction to the gas flow. Furthermore, the valves 212, 222 can be actuated manually by a user or electronically by the patient monitor 206.

A number of alternative embodiments exist for implementing the patient monitoring system 200 without departing from the spirit and scope of the description. For example, the valve 216 can be located in the inflatable cuff 204 or nearby. In addition, the valves 216, 222 can be removed completely. In this embodiment, the patient monitor 206 can actuate the regulator 208 and/or valve 212 to inflate the inflatable cuff 204. When the inflatable cuff 204 is to be deflated, the patient monitor 206 can actuate the regulator 208 and/or valve 212 a second time, as well as actuate the release valve 224. Alternatively, two valves can be used in place of the valve 216. One valve can be used to allow gas to flow from the gas reservoir to the inflatable cuff. The second valve can be used to release gas from the inflatable cuff. The two valves can be actuated independently or at the same time. Furthermore, the two valves can be actuated electronically using the patient monitor 206 or manually by a user.

In addition, the regulator 208 and valve 212 can be implemented using any number of different configurations. For example, regulator 208 and valve 212 can be implemented as two separate devices as shown or as one single device. Alternatively, the patient monitoring system 200 can be implemented using only the regulator 208 and/or the valve 212. In addition, the regulator 208 or any of the valves 212, 216, 222 can further include a pressure gauge to identify the pressure levels of the gas. In addition, the regulator 208 and each valve 212, 216, 222 can communicate with the patient monitor 206 via wired or wireless communication.

As mentioned previously, the inflatable cuff 204 is used to at least partially obstruct an artery of a wearer to measure the wearer's blood pressure. In an embodiment, the inflatable cuff 204 partially obstructs the wearer's artery without occluding, or completely closing, the artery to determine a blood pressure measurement of the wearer.

In one embodiment, the inflatable cuff 204 includes a bladder, a release valve 224 and an attachment mechanism. The bladder contains the gas received from the gas reservoir 202, via the gas pathway and can be made of any material capable of holding gas. For example, the bladder can be made of plastic, cloth, or some other airtight material. Furthermore, the bladder can be configured to hold gas at any number of PSI levels. In one embodiment, the bladder is capable of holding gas at about 4 PSI. However, it is to be understood that the bladder can hold gas at greater than or less than about 4 PSI. An opening in the bladder allows the gas from the gas reservoir to enter exit.

The attachment mechanism allows the inflatable cuff 204 to be attached to a wearer. The attachment mechanism can be made of hook and loop type fasteners, cloth, a clip, flexible materials, water wicking materials, or other material that allows the inflatable cuff 204 to attach to a wearer. The release valve 224 can be actuated manually by a user, electronically by the patient monitor 206, or automatically based on a predefined threshold pressure level. The release valve 224 can be used to release the gas from the inflatable cuff 204 when the pressure reaches a predetermined threshold or unsafe level, or when the inflatable cuff 204 has been inflated above a threshold pressure for a predetermined amount of time.

The sensor 226 can be located on the inside of the inflatable cuff 204, at the patient monitor 206, along the gas pathway segments 210, 214, 218 or along a separate gas pathway segment, as illustrated in FIG. 2. Alternatively, the sensor 226 can be located at the wearer's ear, wrist, finger, or other location. When obtaining blood pressure data from the finger, wrist, or ear less pressure is needed to identify the blood pressure of a wearer, which increases the amount of blood pressure measurements that can be taken by the gas reservoir 202. As mentioned previously, the sensor 226 can be used to collect blood pressure data from the wearer. In an embodiment, the sensor 226 is a pressure sensor capable of measuring the pressure of the inflatable cuff 204 as the inflatable cuff 204 inflates and/or deflates. In another embodiment, the sensor 226 is an auditory sensor used to identify Korotkoff sounds as the inflatable cuff 204 inflates and/or deflates. The cables 228 can be used to communicate the information from the sensor 226 to the patient monitor 206. Alternatively, the sensor 226 can use a wireless transmitter to communicate the blood pressure data to the patient monitor 206.

As mentioned previously, the patient monitor 206 includes a display 230 capable of displaying the diastolic and systolic pressure 232 of the wearer as determined by the patient monitor 206 during inflation and/or deflation. Furthermore, the patient monitor 206 can display the blood pressure measured during inflation and deflation, thereby allowing the user to compare the values. The display 230 of the patient monitor 206 can further be configured to display pressure plots, which can include plots of the blood pressure data 236A and filtered blood pressure data 236B. The plots of the blood pressure data 236A can include the pressure of the inflatable cuff 204 over time, and the plots of the filtered blood pressure data 236B can include the pressure oscillations observed by the sensor, as will be described in greater detail below with reference to FIGS. 3A-3C. In addition, the patient monitor 206 can be configured to display additional physiological parameters 234 as further illustrated on the display device 208. These physiological parameters can include, but are not limited to, heart rate, oxygen saturation, perfusion, glucose measurements, and the like. In addition, the patient monitor 206 can include configuration parameters to control the display 230, as well as the patient monitor 206. Using the configuration parameters, a user can initiate blood pressure measurements of the wearer 218 to control the patient monitor 206.

The patient monitor can also include a user interface for setting or changing the configuration parameters. The configuration parameters can be use to set the frequency and type of blood pressure measurements taken as well as the manner in which to display the measurements. In an embodiment, a periodic or other schedule can be set to obtain measurement; for example, times of day, duration between, or the like may be used to set measurement schedules. In other embodiments, the monitor may monitor other parameters, such for example, oxygen saturations, where a predetermined change in the other parameters triggers a blood pressure measurement.

The configuration parameters can determine how often a blood pressure measurement should be taken, whether it should be taken during inflation, deflation or both. Furthermore the configuration parameters can determine how the patient monitor calculates the blood pressure measurements, such as using the inflationary blood pressure measurements, the deflationary blood pressure measurements, arbitrating between the two, or using a combination such as any a statistical combination of the two or additional measurements like, for example, past measurements. Furthermore, the configuration parameters can determine how the blood pressure measurements should be displayed. For example, the configuration parameters can dictate that only inflationary blood pressure measurements, deflationary blood pressure measurements, the more reliable measurement, or combinations thereof are to be displayed. Furthermore, the configuration parameters can determine if and how the pressure plots, and other physiological parameters are to be displayed.

In addition, the patient monitor 206 can be configured to determine blood pressure measurements while the inflatable cuff 204 is inflating and without occluding the wearer's artery. The patient monitor 206 can be configured to actuate a valve connected to the gas reservoir 202, causing gas to flow from the gas reservoir 202 to the inflatable cuff 204. As the inflatable cuff 204 inflates, the patient monitor 206 can calculate the diastolic pressure and systolic pressure of the wearer 218 using any number of techniques, as described in greater detail below with reference to FIGS. 4A and 4B. For example, the patient monitor 206 can calculate the diastolic pressure and systolic pressure by measuring oscillations of blood flow in an artery or auditory cues as the inflatable cuff 204 inflates and/or deflates. By measuring the wearer's blood pressure during inflation of the inflatable cuff, both the diastolic and systolic pressure can be determined by partially obstructing the wearer's artery and without occluding it. Once the systolic pressure is measured, the patient monitor can actuate the valve 216 or a release valve 224 on the inflatable cuff 204 to release the gas within the inflatable cuff 204.

Figure 3A:
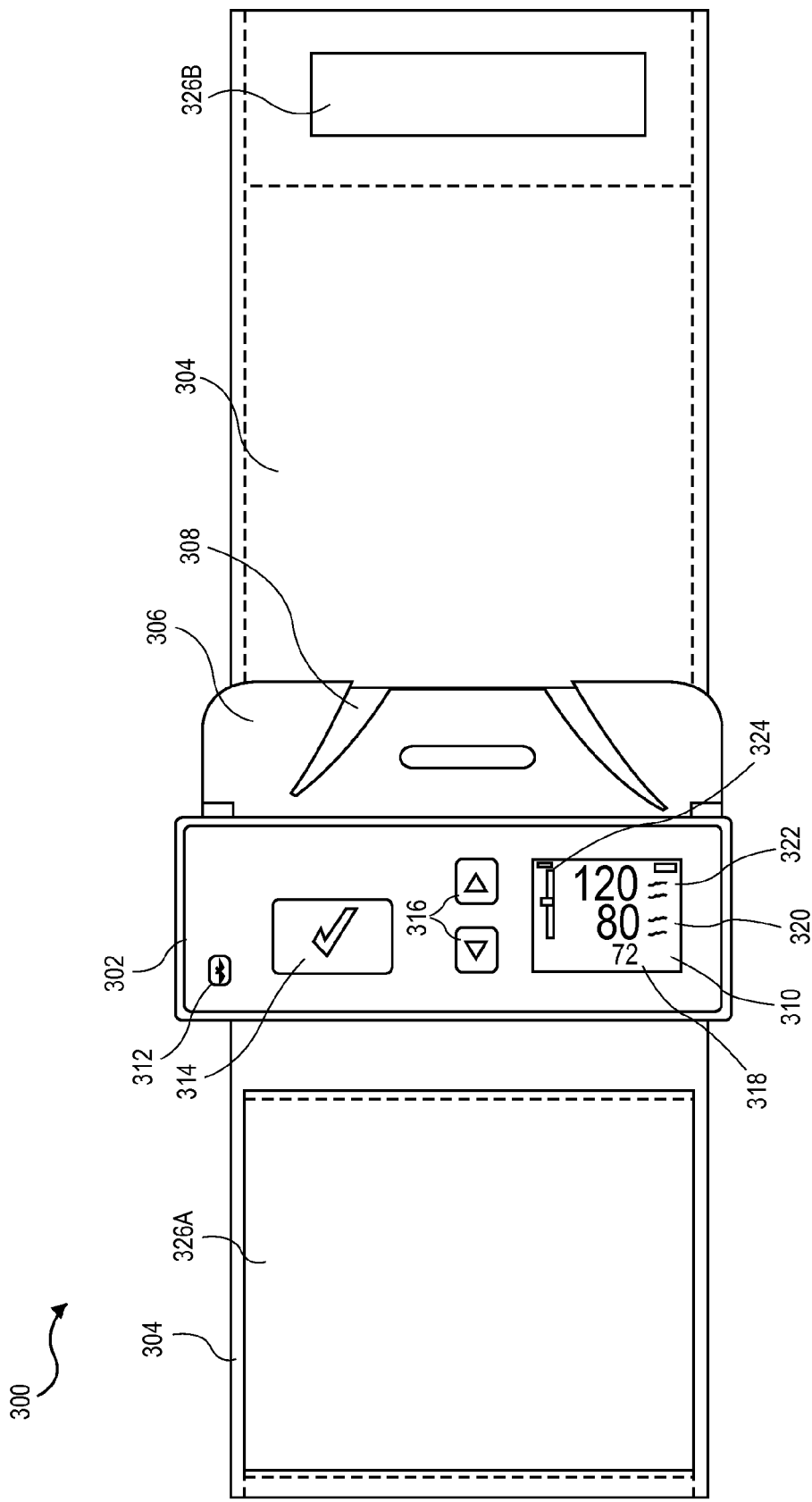

FIGS. 3A-3G illustrate an embodiment of a patient monitoring system 300 configured to be worn by a user. FIG. 3A is a front perspective view of an embodiment of the patient monitoring system 300. The patient monitoring system 300 includes a patient monitor 302, an inflatable cuff 304, and a chamber 306 to retain a gas reservoir 308. The inflatable cuff 304 and chamber 306 can be removably attached to the patient monitor 302. The patient monitor 302, chamber 306, and gas reservoir 308 will be described in greater detail below, with reference to FIGS. 3B-3G.

The inflatable cuff 304 is similar to the inflatable cuffs described in greater detail above, with respect to FIGS. 1A, 1B, and 2. In the illustrated embodiment, the inflatable cuff 304 includes an arm band and can be wrapped around an arm of a user. The inflatable cuff 304 can include one or more attachment surfaces 326A, 326B to maintain the inflatable cuff 304 in a relatively fixed position around the arm of the user. In the illustrated embodiment, the attachment surfaces 326A, 326B are located on either side of the patient monitor 302. In some embodiments, the attachment surfaces 326A, 326B are located on one side of the patient monitor 302, or there is only one attachment surface. The attachment surfaces 326A, 326B can be made from a variety of different materials, such as, but not limited to, hook and loop type fasteners, buttons, snaps, hooks, latches, tape, or other device capable of maintaining the inflatable cuff 304 in a substantially fixed position about the user.

Although not illustrated in FIG. 3A, the patient monitoring system 300 can further include one or more sensors capable of detecting one or more physiological parameters of the user. The sensors can communicate with the patient monitor 302 via wired or wireless communication using a variety of protocols, including, but not limited to, TCP/IP, Bluetooth, ANT, ANT+, USB, Firewire, etc. For example, the patient monitoring system 300 can include one or more pressure sensors, auditory sensors, pulse oximetry sensors, thermometers, accelerometers, and/or gyroscopes. The physiological parameters detected by the various sensors can include, but are not limited to, blood pressure, heart rate, temperature, perfusion, respiration, activity rate, etc. One or more of the sensors can be located within the inflatable cuff 304 or elsewhere on the user. For example, an auditory sensor can be located on the chest of the user to collect respiration data about the user. Another auditory sensor can be located within the inflatable cuff 304 to collect blood pressure data.

Figure 3B:
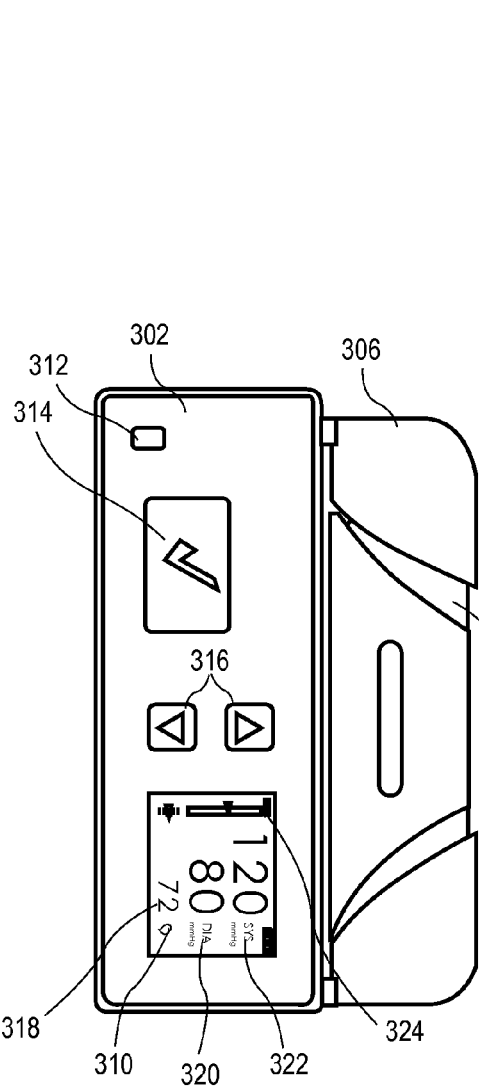

FIG. 3B is a front perspective view of an embodiment of the patient monitor 302 and the chamber 306. In the illustrated embodiment, the patient monitor 302 includes a display 310, a communications link indicator 312, and user interface objects 314, 316. In some embodiments, the patient monitor 302 can further include a power monitor that determines the amount of power remaining for use by the patient monitor 302. When the patient monitor is battery-operated, the power monitor can determine the amount of time or the number of blood pressure measurements that remain before the batteries are to be replaced or recharged.

The patient monitor 302 can be a device dedicated to the measurement of physiological parameters or can be a portable electronic device configured to measure physiological parameters. In some embodiments, the patient monitor 302 is a portable electronic device, such as a smartphone, tablet, or the like, running a program or application configured to calculate physiological parameters based on signals received from the sensors.

The patient monitor 302 receives data from one or more sensors and processes the data to extract physiological parameters of the user. For example, the patient monitor 302 can receive data from a pressure and/or auditory sensor and calculate the patient's blood pressure. In some embodiments, the patient monitor 302 uses accelerometer and gyroscope data to calculate an activity level of the user.

The patient monitor 302 can also provide activity recommendations based on the physiological parameters of the user. For example, the patient monitor can use the patient's height, weight, age, sex, blood pressure readings, heart rate, etc., to recommend a physical activity such as walking, running, or cycling. Furthermore, during an activity the patient monitor 302 can provide recommendations as to whether the patient should increase or decrease their activity levels.

The display 310 is an embodiment of the display 110 described above with reference to FIG. 1A. The display 310 can be implemented using a touch screen, LCD screen, LED screen, or other type of screen and can be used to display one or more physiological parameters, plot diagrams, or user interface information, etc. The display 310 can be any number of different sizes, and in some embodiments, covers a majority of one side of the patient monitor 302. In the illustrated embodiment, the display 310 displays heart rate data 318, blood pressure data 320, 322, and a health indicator 324. However, additional physiological parameters can be displayed, such as, but not limited to, temperature, respiration data, perfusion index data, plethysmograph data, metabolism data, such as calories/hour, etc.

The health indicator 324 can be based on the heart rate data 318, blood pressure data 320, 322, other physiological parameters, or any combination thereof, and can indicate an overall well being of a user. For example, if the patient monitor 302 determines that the blood pressure data 320, 322 is normal, an arrow can point to the middle of the health indicator 324 or the health indicator 324 can be green, etc. If the patient monitor 302 determines that the blood pressure data 320, 322 is high or low, the arrow can point to the top or bottom health or the health indicator 324 can be red or blue, etc. Similarly, other physiological parameters or a combination of physiological parameters can be used by the health indicator 324.

The communication link indicator 312 can be used to indicate whether a communication link is established with one or more devices, such as the sensors, a computer, a portable electronic device, etc. The communication link indicator 312 can change colors or blink depending on the status of the communication link. For example, the communication link indicator 312 can blink during initialization, can turn green once connected, and turn red when a signal is lost or is below a threshold level.

The user interface objects 314, 316 can be implemented using hardware or software. For example, the user interface objects 314, 316 can be buttons or keys, form part of the display 310, or any combination thereof. The user interface objects 314, 316 can be used to interface with the patient monitor 302. For example, the user interface object 314 can be used to select one or more options from the patient monitor 302, such as which physiological parameters to display, how to display the physiological parameters, toggle between which sensors to use, view historical physiological parameter data, etc. In addition, the user interface objects 314, 316 can be used to determine the frequency with which blood pressure measurements should be taken. For example, using the user interface objects 314, 316 the patient monitor 302 can be configured to automatically take blood pressure measurements sequentially as determined by a user, or can be configured to take only one blood pressure measurement before requiring additional input from the user. For example, in some embodiments, by pushing or holding down a user interface object, the patient monitor 302 will automatically toggle between a single measurement mode and a sequential measurement mode. Furthermore, the user interface objects 316 can be used to scroll through one or more options displayed on the display 310. Other user interface objects can be used as desired.

With continued reference to FIG. 3B, the chamber 306 can be in physical contact with the patient monitor 302. In some embodiments, the patient monitor 302 fits into a pre-formed case, which also contains the chamber 306. In certain embodiments, the patient monitor 302 includes attachment mechanisms to connect with the chamber 306. The attachment mechanisms can include, but are not limited to, clips, screws, screw holes, bars, snaps, buttons, and the like. The gas reservoir 308 fits into the chamber 308 as illustrated and as will be described in greater detail with reference to FIG. 3C. Furthermore, the chamber 306 can be adjusted to fit different sized gas reservoirs 308.

Figure 3C:
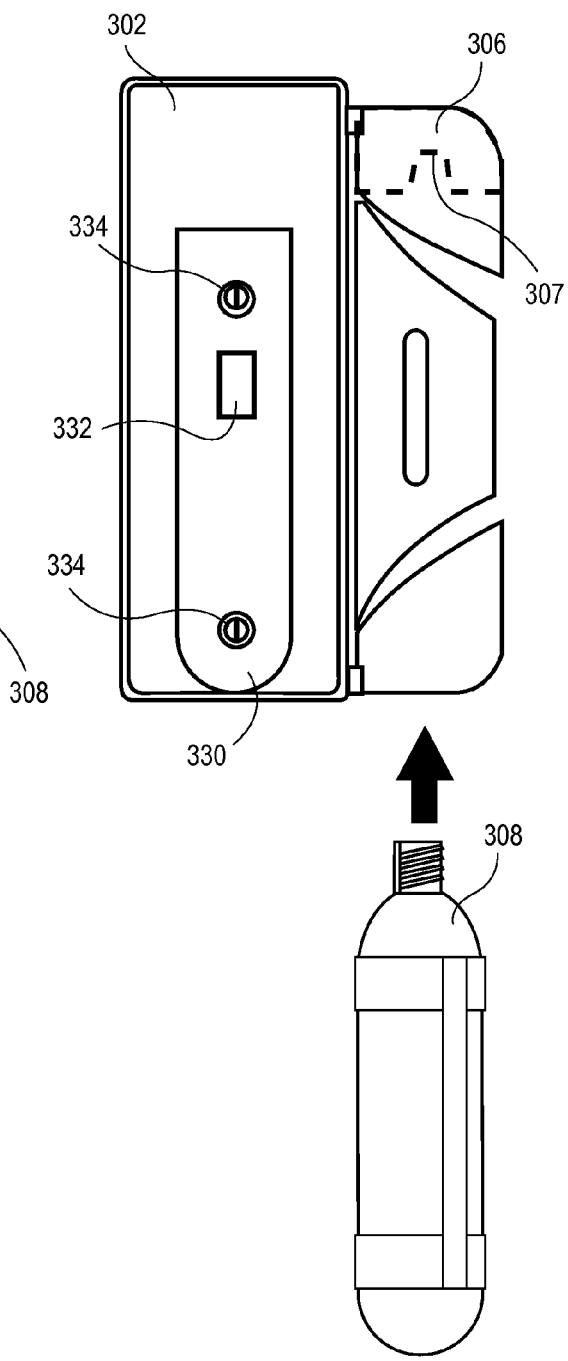

FIG. 3C is a back perspective view of the patient monitor 302 and chamber 306. The illustrated embodiment further includes a gas reservoir interface 307 as part of the chamber 306. The gas reservoir interface 307 interacts with the gas reservoir 308 to maintain the gas reservoir within the chamber 306. The gas reservoir interface 307 can include a locking mechanism that prevents the use of unapproved or unauthorized gas reservoirs 208. The locking mechanism can be a mechanical or electronic locking mechanism.

A mechanical locking mechanism can include many forms, such as threads, a clamp, lock and key designs, etc. For example, in some embodiments, the gas reservoir interface 307 can includes threads that complement threads of the gas reservoir 308. Accordingly, the gas reservoir 308 can be screwed into the chamber 306 using the gas reservoir interface 307. In some embodiments, gas reservoirs 308 that include a different number of threads, a different design of threads, or that do not include threads will not properly interface with the gas reservoir interface 307. In certain embodiments, a clamp can act as the locking mechanism to keep the gas reservoir 308 in place. In certain embodiments, the mechanical locking mechanism can be in the form of a proprietary connector. The gas reservoir interface 307 can include a particular physical layout that is uniquely designed to interface with approved or authorized gas reservoirs 308, similar to a lock and key design.

The locking mechanism can also be implemented as an electronic locking mechanism. The electronic locking mechanism of the gas reservoir interface 307 can include an electronic interface that allows the patient monitor 302 to communicate with the gas reservoir 308. The electronic interface can include a memory chip, processor, RFID, resistor, or other circuit elements that can interface with electronics on the gas reservoir 308. Authorized or approved gas reservoirs 308 can include the circuit elements that can unlock the electronic locking mechanism of the gas reservoir interface 307 and allow the gas reservoir 308 to be used with the patient monitor 302.

The illustrated embodiment also includes an interface 330 attached to the patient monitor 302 and used to maintain the patient monitor 302 in close proximity to the inflatable cuff 304. The recess 332 of interface 330 can complement a portion of the cuff 304 to lock the patient monitor 302 in place with the cuff 304. Screws 334 can be used to maintain the interface 330 attached to the patient monitor 302.

FIGS. 3D and 3E are side perspective views of the patient monitor 302 and chamber 308. FIGS. 3F and 3G are top and bottom perspectives of the patient monitor and chamber 308, respectively. With reference to FIG. 3G, the patient monitor 302 can include an electronic interface 336, such as a USB or mini-USB port. The electronic interface 336 can be used to communicate with another electronic device, such as a computer or portable electronic device. FIG. 3G further illustrates that the chamber 306 can be rotated forwards and backwards as desired. For example, the chamber 306 can be physically attached to the patient monitor 302 via a pivot that allows the chamber 306 to swing about one or more axes. The pivot can be implemented using a hinge, ball-and-socket joint, link, pin, spring, swivel, bolt, and the like. The pivot can also include a locking mechanism that can lock the chamber 306 in a certain position with respect to the patient monitor 302. The locking mechanism can be implemented using a clamp, ratchet, pin, grooves within a link, pin, spring, or bolt, and the like. In this way, the chamber 306 can be rotated to a preferred position and then locked in place for use. For example, a user can adjust the chamber 306 so that it fits snugly against their arm, or other limb, and then lock the chamber in that position so that it stays in its position when the user moves.

Figure 4A:
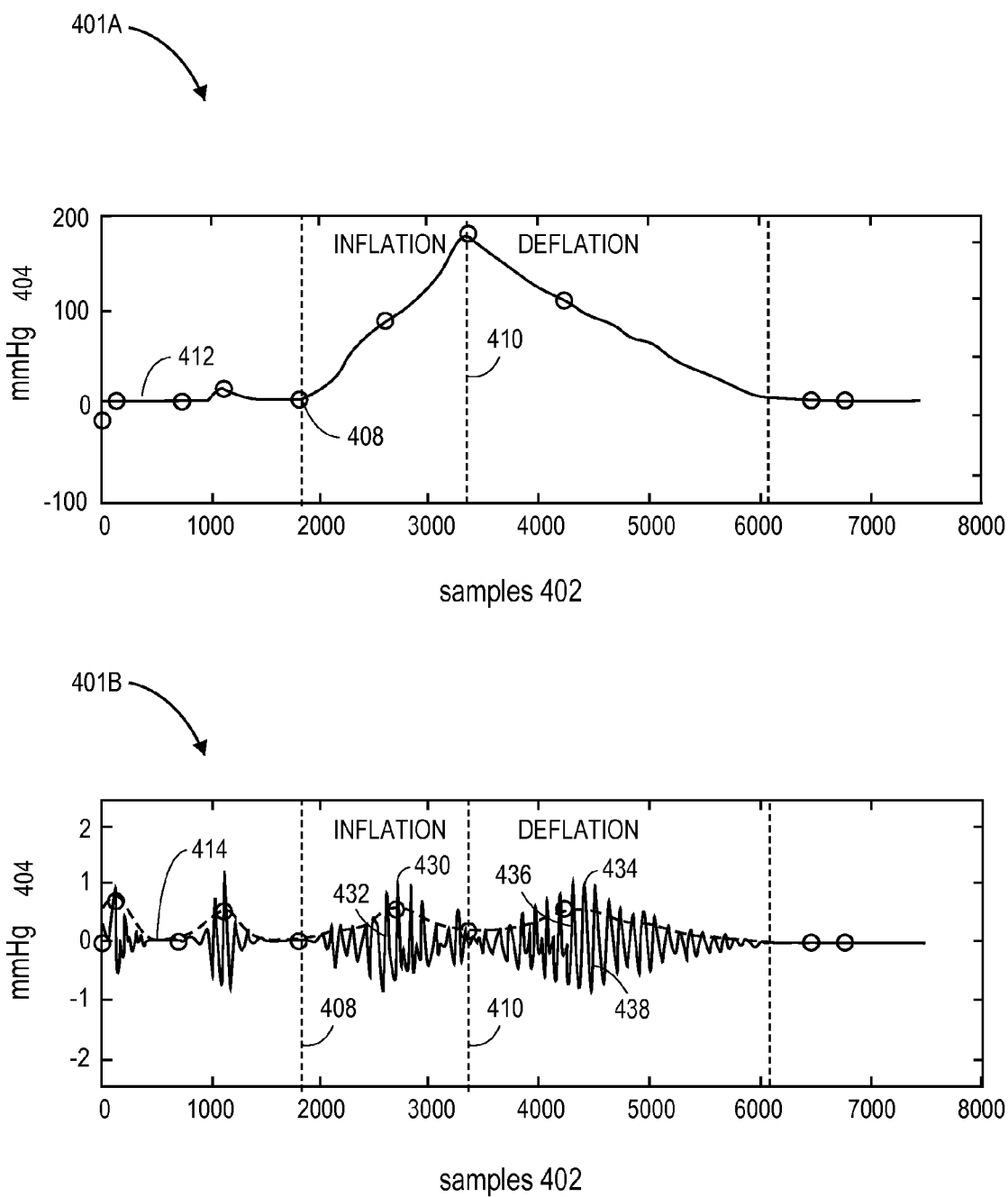
FIGS. 4A-4C are plot diagrams illustrating embodiments of pressure variations of an inflatable cuff associated with a wearer during blood pressure measurement.

As mentioned previously, the display 230, can be configured to display additional information regarding the wearer. FIGS. 4A-3C are plot diagrams illustrating embodiments of various plots that can be displayed by the display 230, 310. The plots in FIGS. 4A-3C are plot diagrams illustrating some embodiments of the pressure at the inflatable cuff 204, including the oscillations of pressure, observed by the sensor 226 during inflation and deflation.

Plot 401A is a plot diagram illustrating an embodiment of the pressure of the inflatable cuff 204 during inflation and deflation, which can also be referred to as blood pressure data. The x-axis of plot 401A represents the number of samples taken by the patient monitor 206 over time. The patient monitor 206 can be configured to take samples at any number of increments to achieve a desired data resolution. For example, the patient monitor 206 can sample the inflatable cuff every second, millisecond, microsecond, etc. Although illustrated in increments of samples, time can also be used for the x-axis 402. The y-axis 404A of plot 401A represents the pressure level, in mmHg, of the inflatable cuff 204. The line 412 represents the pressure level of the inflatable cuff 204 over time.

Prior to point 408, signals on the line 412 represent electronic noise caused by the environment or the patient monitoring system 200. At point 408, the valve 216 is actuated. The valve 216 can be actuated electronically by the patient monitor 206 or manually by a user. Once actuated, gas from the gas reservoir 202 begins to inflate the inflatable cuff 204 at a rate determined by a user electronically using the patient monitor 206 or manually using the regulator 208 and/or valve 212. In one embodiment, the inflation rate is an approximately constant rate, which leads to an approximately constant increase in pressure in the inflatable cuff. The sensor 226 reads the rise in pressure in the inflatable cuff 204, as indicated by the rise in line 412 of the plot 401A. Thus, from point 408 to point 410, the inflatable cuff is in an inflation mode and is inflating.

At point 410, the valve 216 is actuated again, ending the inflation of the inflatable cuff 204. Although illustrated at 200 mmHg, the point 410 can be located at any desired pressure level. In one embodiment, the 216 valve is actuated when the measured pressure level within the inflatable cuff 204 is greater than the expected systolic pressure of the wearer. The expected systolic pressure of the wearer can be determined by previous blood pressure measurements, historical information, clinical data from one or more wearers, or the like. In one embodiment, the point 410 changes between blood pressure measurements. For example, the inflatable cuff can be configured to inflate to 200 mmHg for the first measurement. If it is determined during the first measurement that the wearer's systolic pressure is measurably less than 200, then during the proximate measurement, the inflatable cuff 204 can be inflated to a lower pressure. Varying the pressure level to which the inflatable cuff 204 inflates can conserve gas. Likewise, if the wearer's measured systolic pressure is greater than the expected systolic pressure, the inflatable cuff 204 can be inflated to a greater pressure during the proximate measurement. Alternatively, the valve 216 can be actuated once the inflatable cuff 204 reaches any desired or predefined pressure level, such as 160 mmHg, 200 mmHg, 400 mmHg, etc.

In some embodiments, in addition to ending the inflation of the inflatable cuff, actuating the valve 216 also begins a deflation mode of the inflatable cuff. For example, actuating the valve 216 can close the gas pathway between the gas reservoir 202 and the inflatable cuff 204 and open the gas pathway between the inflatable cuff 204 and ambient air, allowing the gas to exit the inflatable cuff 204. Once the valve 216 is actuated, the inflatable cuff 204 deflates leading to a decrease in pressure within the inflatable cuff 204. Actuating the valve 216, as well as the valve 222 can be configured so that the pressure within the inflatable cuff 204 decreases at any desired rate. In one embodiment, the pressure within the inflatable cuff 204 decreases at an approximately constant rate. Additional blood pressure measurements can be taken during the deflation of the inflatable cuff 204, as described in greater detail below with reference to FIGS. 5A and 5B.

The patient monitor 206 can calculate the blood pressure of the wearer at any time during inflation and/or deflation, once it has received sufficient blood pressure data. In some embodiments, the patient monitor 206 can calculate the diastolic pressure followed by the systolic pressure during inflation of the inflatable cuff 204. In certain embodiments, the patient monitor can calculate both diastolic and systolic pressure simultaneously once the valve 216 is actuated or during inflation, once the patient monitor 206 has sufficient blood pressure data. The patient monitor 206 can alternatively wait until additional measurements are taken during the deflation of the inflatable cuff 204 before calculating the diastolic and systolic pressure. In this way, the patient monitor can compare or arbitrate the diastolic and systolic measurements during inflation and deflation of the inflatable cuff 204 to achieve greater reliability in the measurements.

With continued reference to FIG. 4A, the plot 401B is a plot diagram illustrating an embodiment of the change in pressure in the inflatable cuff 204 due to blood flow in the artery during inflation and deflation of the inflatable cuff 204. In one embodiment, the line 414 is obtained by filtering the plot 401A and normalizing the data based on the change in pressure due to the inflation and deflation of the inflatable cuff 204 and can be referred to as filtered blood pressure data. The plot 401B of the pressure oscillations due to the blood flow in the artery of the wearer, or filtered blood pressure data, can be displayed on the display 230, 310 along with the plot 401A, the blood pressure readings, and/or other physiological parameters. Similar to plot 401A, the x-axis 402 of plot 401B represents the number of samples taken by the patient monitor 206 over time. The y-axis 404B of plot 401B represents normalized changes in pressure in the inflatable cuff 204.

As illustrated in the plot 401B, when the valve 216 is actuated at point 408, the inflatable cuff 204 inflates and exerts pressure against the wearer's artery. As the inflatable cuff 204 exerts pressure against the wearer's artery, the sensor 226 is able to detect the variations in pressure in the inflatable cuff 204 due to blood flow within the artery, which are also referred to as pressure variations or pressure oscillations. The pressure oscillations are illustrated in plot 401A as small deviations or bumps in the line 412.

As further illustrated by the plot 401B, as the inflatable cuff 204 continues to inflate, the artery becomes increasingly obstructed, leading to greater pressure variations observed by the pressure sensor, which leads to greater oscillations in the line 414. With continued inflation of the inflatable cuff, the variations in pressure eventually begin to decrease as the blood flow becomes occluded. At point 410, the pressure exerted by the inflatable cuff completely occludes the artery. As mentioned previously, in one embodiment, once the artery is occluded, the valve 216 is actuated allowing the gas to exit the inflatable cuff 204 and the inflatable cuff 204 to deflate. In another embodiment, the valve 216 is actuated prior to the occlusion of the artery.

As further illustrated by the plot 401, as the inflatable cuff 204 begins to deflate, the oscillations of the pressure observed by the pressure sensor 226 again begin to increase significantly as blood flow in the artery increases. As the inflatable cuff 204 further deflates, the pressure exerted on the artery decreases leading to a decrease in pressure variation observed by the pressure sensor 226. Eventually, the inflatable cuff 204 exerts little to no pressure on the artery, and the blood flow in the artery has little to no effect on the pressure in the inflatable cuff 226. The patient monitor 206 uses the characteristics of the oscillations of pressure due to blood flow through an artery of the wearer, such as the slope of the oscillations and/or the magnitude or amplitude of the oscillations, to determine the blood pressure. The patient monitor 206 can use the blood pressure data obtained during inflation and/or deflation of the inflatable cuff to determine the blood pressure.

In one embodiment, to determine the blood pressure during inflation, the patient monitor identifies the pressure in the inflatable cuff at which the largest magnitude oscillation, also referred to as the maximum deflection point or largest amplitude oscillation, during inflation is detected. In the illustrated embodiment, the pressure monitor identifies the largest magnitude oscillation at point 430. The pressure in the inflatable cuff at which the largest magnitude oscillation during inflation is detected approximately coincides with the systolic blood pressure of the wearer. In one embodiment, the patient monitor also identifies the pressure in the inflatable cuff at which the largest slope in the oscillations prior to the largest magnitude oscillation during inflation is detected. In the illustrated embodiment, the pressure monitor identifies the largest slope in the oscillations prior to the largest magnitude oscillation at point 432. The largest slope in the oscillations prior to the largest magnitude oscillation during inflation approximately coincides with the diastolic pressure of the wearer.

In addition, the patient monitor can determine the blood pressure of the wearer during deflation. In one embodiment, to determine the blood pressure during deflation, the patient monitor identifies the largest magnitude oscillation during deflation (point 434 in the illustrated embodiment). The patient monitor further identifies the pressure in the inflatable cuff at which the largest slope in the oscillations prior to the largest magnitude oscillation during deflation is detected (point 436 in the illustrated embodiment). The largest slope in the oscillations prior to the largest magnitude oscillation during deflation approximately coincides with the systolic pressure of the wearer. The patient monitor also identifies the pressure in the inflatable cuff at which the largest slope in the oscillations after the largest magnitude oscillation during deflation (point 436 in the illustrated embodiment). The largest slope in the oscillations after the largest magnitude oscillation during approximately deflation coincides with the diastolic pressure of the wearer.

A number of alternate methods exist for determining blood pressure during inflation and deflation of the inflatable cuff. For example, during deflation the patient monitor can calculate the systolic blood pressure as the pressure at which the oscillations become detectable and the diastolic pressure as the pressure at which the oscillations are no longer detectable. Alternatively, the patient monitor can calculate the mean arterial pressure first (the pressure on the cuff at which the oscillations have the maximum amplitude). The patient monitor can then calculate the diastolic and systolic pressures based on their relationship with the mean arterial pressure. Additional methods can be used without departing from the spirit and scope of the description. For example, pressure values at locations other than the largest magnitude oscillation or maximum deflection point and largest slope can also be used.

Plots 401A and 401B further illustrate the potentially adverse effect signal noise can have on the blood pressure measurements. As illustrated, signal noise is detected at least twice in line 414 prior to inflation. The detected signal noise in at least one instance exceeds the maximum deflection point during inflation. In addition, the signal noise may also contain the largest slope prior to the maximum deflection. In either event, if the signal noise is not accounted for, the patient monitor 206 is in danger of calculating diastolic and systolic pressures of the wearer at points other than during inflation or deflation. In some embodiments, based on the amount and magnitude of signal noise detected, the patient monitor can assign confidence levels to the blood pressure measurements. Based on line 414, the patient monitor 206 can place a lower confidence level in the blood pressure measurement during inflation due to the observed signal noise.

As mentioned above, the plots 401A, 401B can both be displayed on the display 230, 310 of the patient monitor 206, 302. The plots 401A, 401B can be displayed simultaneously or consecutively. In addition the plots 401A, 401B can be displayed along with the diastolic pressure and systolic pressure as measured by the patient monitor 206. Furthermore, the measured diastolic pressure and systolic pressure during inflation can be displayed along with the measured diastolic pressure and systolic pressure during deflation. In addition, the patient monitor 206 can further display additional physiological parameters measured by the patient monitor 206.

Figure 4B:
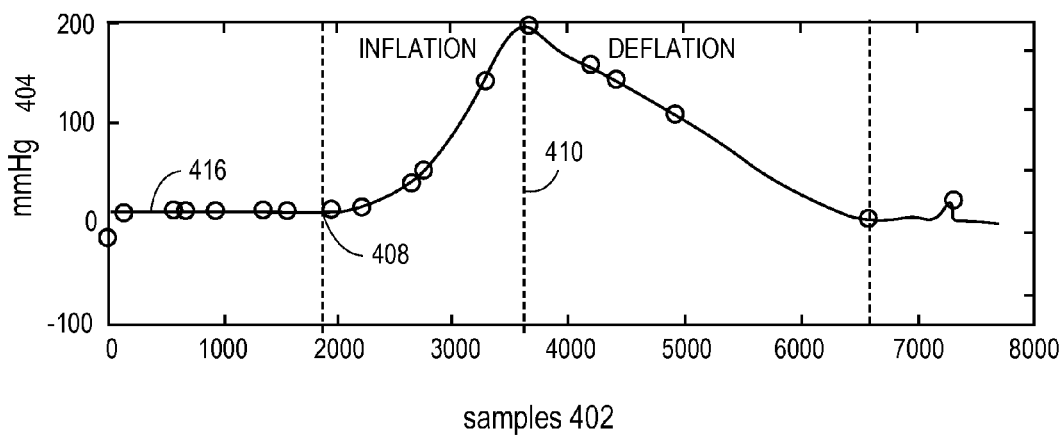
Figure 4B:
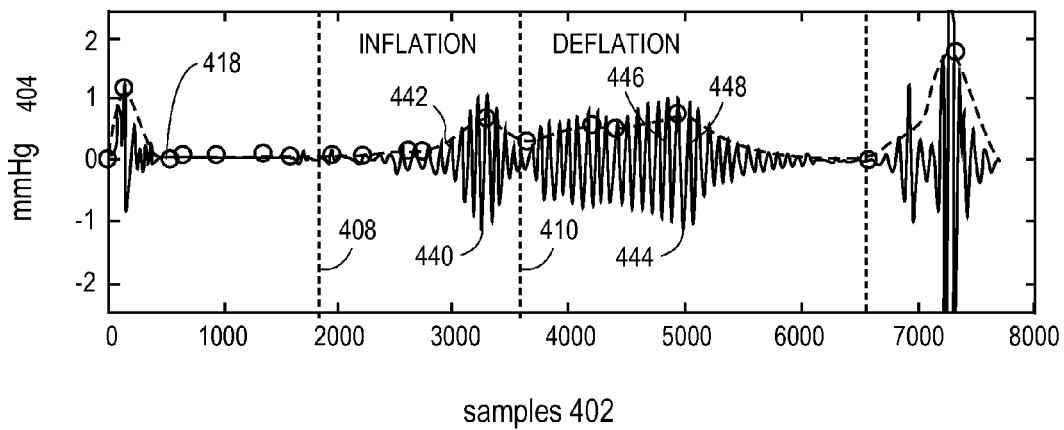
Figure 4C:
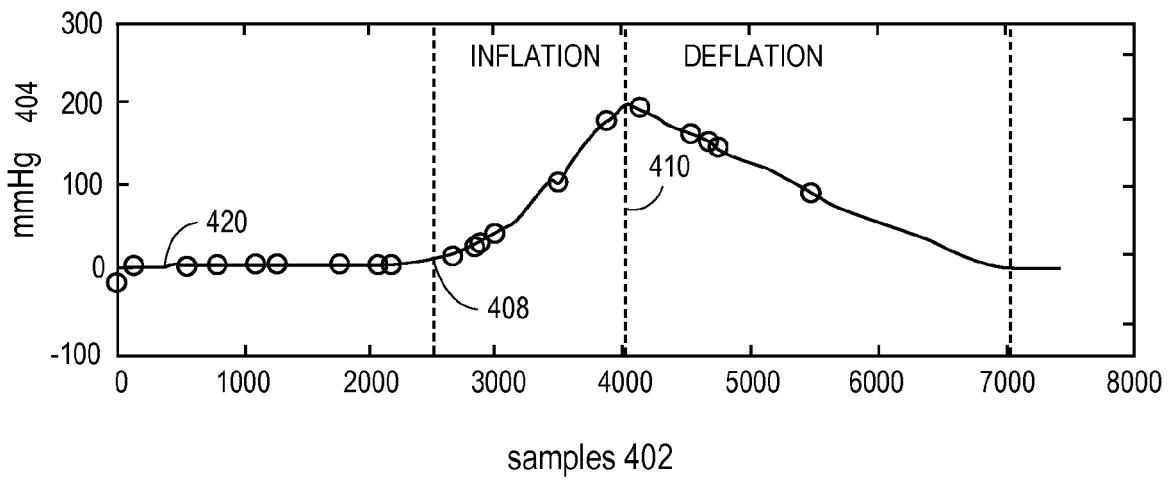
Figure 4C:
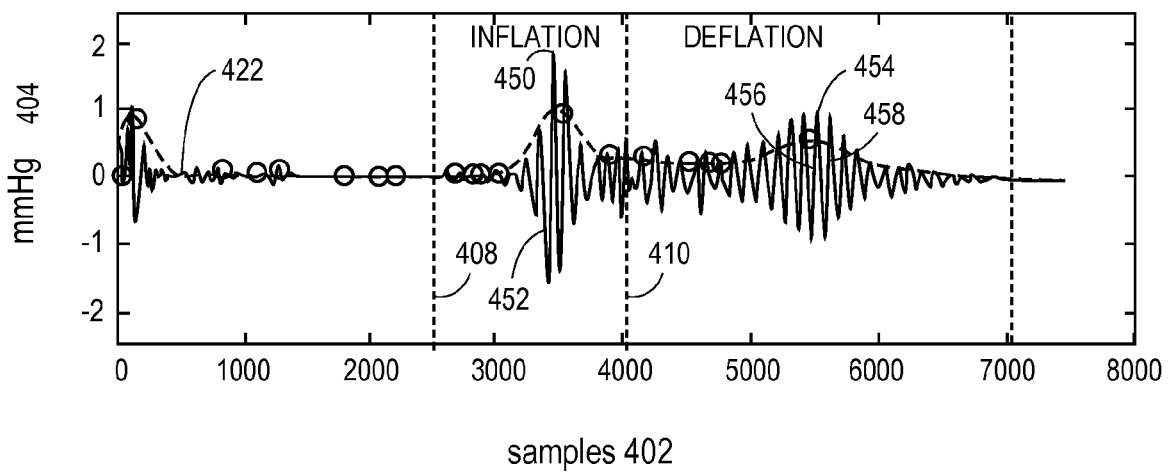

FIGS. 4B and 4C include plot diagrams illustrating additional embodiments of the pressure of the inflatable cuff 204 during inflation and deflation. Plots 403A and 405A correspond to plot 401A, and plots 403B and 405B correspond to plot 401B. Similar to plots 401A and 401B, plots 403A, 403B, 405A, and 405B illustrate the inflation of the inflatable cuff 204 beginning at point 408 and ending at point 410. In addition the deflation of the inflatable cuff begins at point 410 in plots 403A, 403B, 405A, and 405B.

Plots 403A and 403B further illustrate signal noise being exhibited at different points throughout the lines 416 and 418. The first observed signal noise occurs near the beginning of the lines 418 and another occurs near the end. Similar to the oscillations due to blood flow in the artery, signal noise is exhibited as small displacements on the line 416 and oscillations in the line 418. As illustrated, unless accounted for, the signal noise occurring in plots 403A and 403B can have an adverse affect on blood pressure measurements due at least to their magnitude. The first detected signal noise results in the maximum deflection point prior to deflation and the last detected signal noise results in the maximum deflection point after deflation. In embodiments, where maximum deflection points are used, if inflation and deflation are not demarcated appropriately or if signal noise is not accounted for, the patient monitor 206 can erroneously determine the blood pressure measurements based on the signal noise.

The plot 403B further illustrates an example where a blood pressure measurement taken during inflation can in some instance have a higher confidence level than the blood pressure measurement taken during deflation. As mentioned previously, during inflation, the diastolic pressure can be determined as the pressure at which the largest slope in line 418 prior to the maximum deflection point during inflation occurs (point 442 in the illustrated embodiment). The systolic pressure can be calculated as the pressure at which the maximum deflection point of line 418 occurs during inflation (point 440 in the illustrated embodiment). Upon deflation, the systolic pressure is calculated as the pressure at which the largest slope in line 418 prior to the maximum deflection point (point 444 in the illustrated embodiment) during deflation occurs (point 446 in the illustrated embodiment). Similarly, the diastolic pressure is calculated as the pressure at which the largest slope in line 418 after the maximum deflection point during deflation occurs (point 448 in the illustrated embodiment). As illustrated in plot 403B, the maximum deflection point during deflation can be difficult to identify, which can make it difficult to calculate the diastolic and systolic pressure of the wearer accurately. Accordingly, the confidence placed in the blood pressure measurement during deflation can be relatively low compared to the confidence level placed in the blood pressure measurement during inflation. Accordingly, the patient monitor 204 can determine that the blood pressure measurement taken during inflation is likely more accurate. In addition, depending on the amount and magnitude of the signal noise detected, the patient monitor 206 can determine that neither blood pressure measurement reaches a threshold confidence level and that blood pressure measurements should be retaken.

Plots 405A and 405B illustrate yet another example of blood pressure measurements taken during inflation and deflation of the inflatable cuff 204. As illustrated, signal noise is detected near the beginning of lines 420 and 422, resulting in oscillations observed in line 422. As mentioned previously, if not accounted for, the signal noise can adversely affect the blood pressure measurements during inflation. However, in the line 422, the maximum deflection point prior to deflation occurs during inflation. Thus, the signal noise at the beginning of the line 422 should not affect the blood pressure measurements. Plots 405A and 405B further illustrate an example where the blood pressure measurement taken during inflation can have a similar confidence level as the confidence level of the blood pressure measurement taken during deflation. As illustrated, the line 418 exhibits a distinctive maximum amplitude during inflation (point 450 in the illustrated embodiment) and during deflation (point 454 in the illustrated embodiment). In the illustrated embodiment, the patient monitor calculates the largest slope during inflation as the slope at point 452. During deflation, the patient monitor calculates the largest slop prior to the maximum amplitude at point 456 and the largest slop following the maximum amplitude at point 458.

Figure 5A:
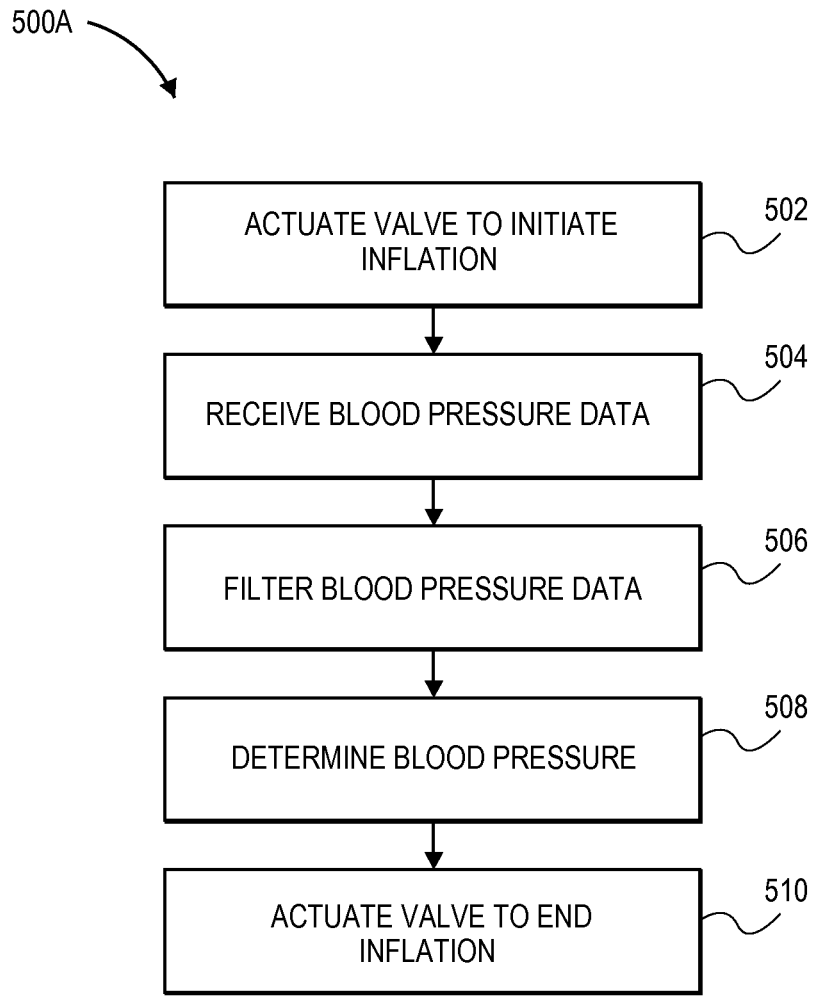
FIGS. 5A and 5B are flow diagrams illustrating embodiments of a process implemented by a patient monitor for measuring the blood pressure of a wearer.

FIG. 5A is a flow diagram illustrating an embodiment of a process 500A for measuring blood pressure during inflation of an inflatable cuff 204. As illustrated in FIG. 5A, the process 500A begins at block 502 by actuating a valve, which allows gas to flow from a gas reservoir 202 to the inflatable cuff 204, causing the inflatable cuff 204 to inflate. The valve can be located near an opening of the gas reservoir 202, at some point along the gas pathway or at the inflatable cuff 204. In one embodiment, multiple valves 212, 216 and/or regulators 208 can be included between the gas reservoir 202 and the inflatable cuff 204. Each valve and/or regulator can be actuated prior to inflating the inflatable cuff 204. The valve(s) can be actuated manually by a user or electronically by a patient monitor 206. For example, a user can manually open the valve 216 to allow gas to flow from the gas reservoir 202 to the inflatable cuff 204. The user can open the valve in a way that allows for the inflation of the inflatable cuff 204 at an approximately constant rate of inflation. A regulator 208 can also be used to achieve the approximately constant rate of inflation. Alternatively, a patient monitor 206 in communication with the gas reservoir can actuate the valve 216, allowing the gas to flow from the gas reservoir 202 to the inflatable cuff 206. Communication from the patient monitor 206 can occur by wired or wireless communication, such as a LAN, WAN, Wi-Fi, infra-red, Bluetooth, radio wave, cellular, or the like, using any number of communication protocols.

To actuate the valve, an input to the patient monitor 206 such as a button can be used. Alternatively, the patient monitor can automatically actuate the valve once the patient monitor is turned on or based on one or more configuration parameters. For example, the patient monitor can be configured to determine the blood pressure of a wearer once every time period. The timer period can be configured as any period of time, such as 6 minutes, 15 minutes, 60 minutes, etc. In yet another embodiment, the patient monitor 206 determines if the inflatable cuff is attached to a wearer. If the patient monitor 206 determines that the inflatable cuff is attached to a wearer, the patient monitor 206 can actuate the valve at predefined time intervals. Any number of methods can be used to determine if the inflatable cuff is attached to a wearer. For example, the patient monitor 206 can determine whether the inflatable cuff is attached to a wearer using infra-red sensors, pressure sensors, capacitive touch, skin resistance, processor polling or current sensing or the like.

Once the inflatable cuff 204 is inflating, the patient monitor 206 receives blood pressure data from the sensors, as illustrated in block 504. The blood pressure data can be obtained at the inflatable cuff 204 using any number of different sensors or methods. For example, a pressure sensor can be used to identify the air pressure due to the inflation and deflation of the inflatable cuff 204. The pressure sensor can be located at the inflatable cuff, the patient monitor 206, at some point along the gas pathway, or some other location where it is capable of measuring the pressure of the inflatable cuff 204. Alternatively, an auditory sensor communicatively coupled to the patient monitor 206 can be used to detect Korotkoff sounds, similar to the method used for manual determination of blood pressure using a stethoscope.

At block 506, the patient monitor 206 filters the blood pressure data. Filtering the blood pressure data can reduce the effects of, or completely remove, environmental noise and/or the electrical noise found within the patient monitoring system. Furthermore, during filtering, the patient monitor 206 can normalize the blood pressure data to account for the changes in pressure due to the inflation and deflation of the inflatable cuff. In one embodiment, after filtering the blood pressure data, only the pressure oscillations in the inflatable cuff 204 due to blood flow in an artery of the wearer remain, and in some instances signal noise. Upon filtering the blood pressure data, the patient monitor 206 can determine the blood pressure of the wearer, as illustrated in block 508.

The patient monitor 206 can determine the blood pressure using any number of different methods as described above with reference to FIGS. 4A-3C. For example, the patient monitor 206 can determine the blood pressure of the wearer using the slopes and/or amplitude of the pressure oscillations, the mean arterial pressure, and/or the Korotkoff sounds.

Once the patient monitor 206 determines the blood pressure of the wearer, the patient monitor 206 can actuate a valve to stop gases from flowing from the gas reservoir to the inflatable cuff, as illustrated in block 510. In one embodiment, the valve is a three-way valve 216 and actuating the valve to stop the gases from flowing from the gas reservoir to the inflatable cuff also opens the gas pathway segment 220 to release the gas from the inflatable cuff.

Fewer, more, or different blocks can be added to the process 500A without departing from the spirit and scope of the description. For example, the patient monitor 206 can filter the blood pressure data to determine the diastolic pressure first. As the diastolic pressure is being calculated, the patient monitor 206 can continue receiving and filtering the blood pressure data to determine the systolic pressure. In an embodiment, the patient monitor can determine the blood pressure without filtering the blood pressure data. In addition, a user can determine the blood pressure measurements without the use of the patient monitor 206. In an embodiment, a user using a stethoscope can determine the diastolic and systolic pressure during inflation of the inflatable cuff without filtering the blood pressure data.

As mentioned previously, by measuring the blood pressure during inflation of the inflatable cuff 204, the blood pressure of the wearer can be measured in less time and using less pressure. Furthermore, because the artery is occluded for less time, or not occluded at all, the blood pressure can be measured more frequently.

Figure 5B:
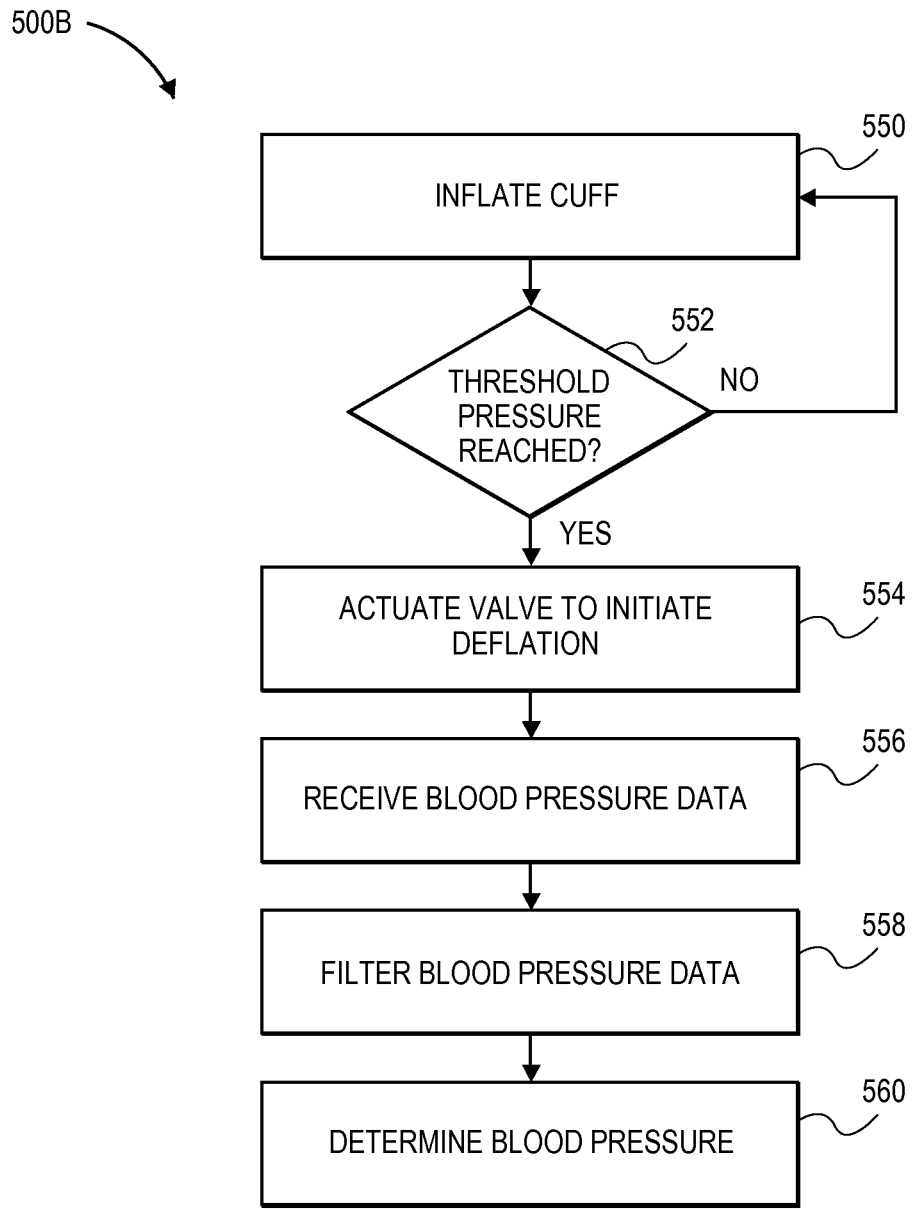

FIG. 5B illustrates a flow diagram of a process 500B for measuring blood pressure during deflation of an inflatable cuff. At block 550, the inflatable cuff 204 is inflated. In one embodiment, the inflatable cuff 204 is inflated using gas from a gas reservoir 202. Using the gas from the gas reservoir 202, the inflatable cuff 204 can be inflated very quickly leading to a relatively short wait time before blood pressure measurements can be taken.

As the inflatable cuff 204 inflates, the patient monitor determines whether a threshold pressure has been reached, as illustrated in block 552. The threshold pressure can be any pressure level and can vary between blood pressure measurements. Furthermore, the threshold pressure can be determined based on previous blood pressure measurements, historical information, clinical data from one or more wearers, or the like. In one embodiment, the threshold pressure is above an expected systolic pressure of the wearer. In another embodiment, the threshold pressure is above an expected occlusion pressure or the pressure at which the artery is occluded. The inflation can be initiated in a manner similar to that described above with reference to FIG. 5A. If the patient monitor 206 determines that the threshold pressure has not been reached, the inflatable cuff 204 continues to inflate. However, if the patient monitor 206 determines that the threshold pressure has been reached, the process moves to block 554.

At block 554, the patient monitor 206 actuates the valve to initiate deflation of the inflatable cuff 206. In one embodiment, the valve is a three-way valve similar to valve 216 of FIG. 2, such that the inflation of the inflatable cuff 204 ends at the same time deflation begins. Once the deflation of the inflatable cuff 204 begins, the process moves to block 556 and the patient monitor receives blood pressure data, filters the blood pressure data 558, and determines blood pressure 560. Greater detail regarding receiving blood pressure data 556, filtering the blood pressure data 558 and determining blood pressure is described above with reference to blocks 504-408 of FIG. 5A.

Fewer, more, or different blocks can be added to the process 500B without departing from the spirit and scope of the description. For example, the patient monitor 206 can determine the systolic pressure prior to receiving the blood pressure data or filtering the blood pressure data to determine the diastolic pressure. In addition, the process 500B can be implemented without the use of the patient monitor 206. For example, a user can receive blood pressure data via a stethoscope. The user can determine the blood pressure of the wearer using Korotkoff sounds, and can also determine the blood pressure of the wearer without filtering the blood pressure data. Furthermore, process 500A and 500B can be combined and measurements taken during inflation and deflation of the inflatable cuff. Furthermore, the measurements taken during deflation of the inflatable cuff can be used to verify the blood pressure readings taken during inflation of the inflatable cuff 204.

Figure 6:
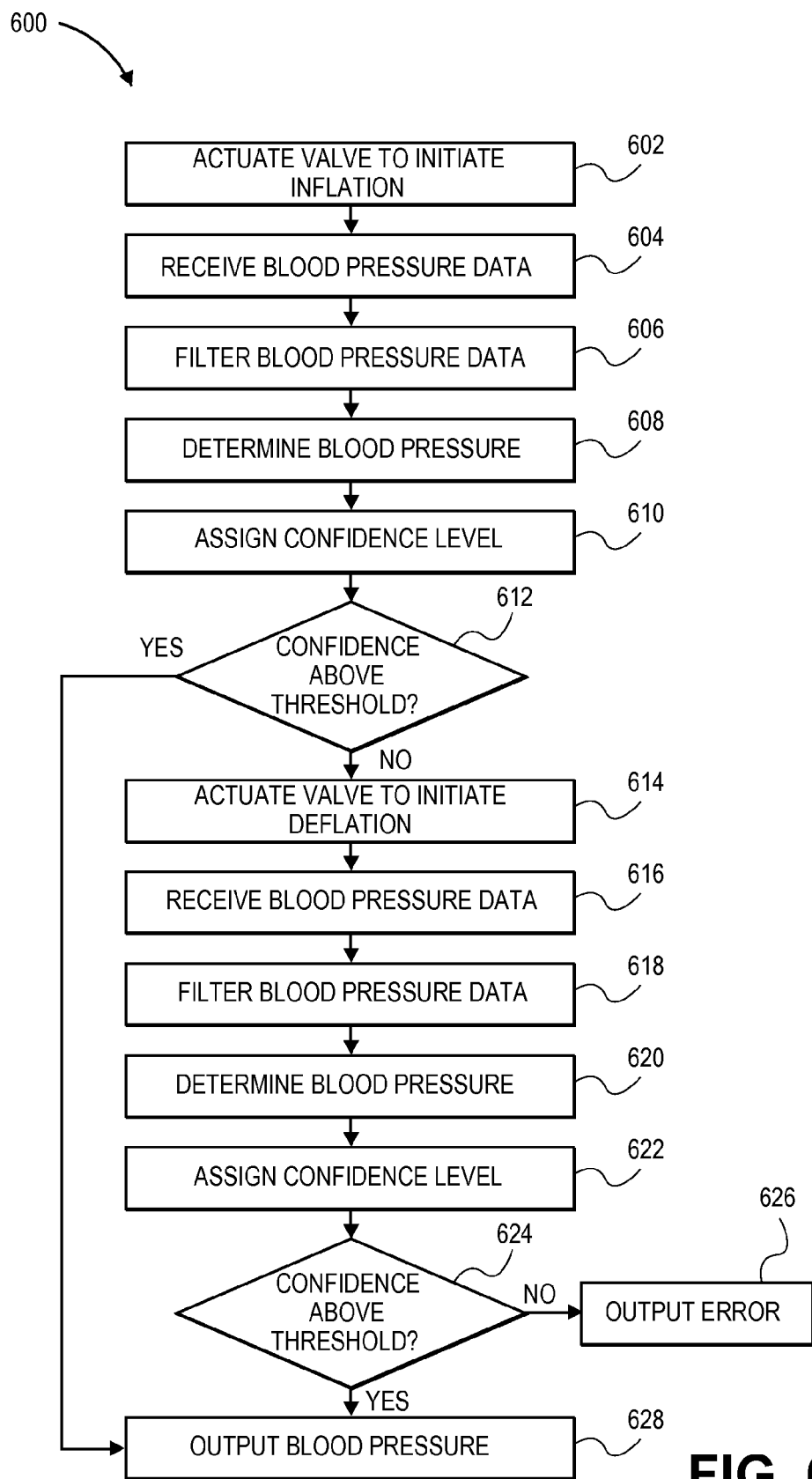
FIG. 6 is a flow diagram illustrating another embodiment of a process implemented by the patient monitor for measuring blood pressure of a wearer.

FIG. 6 is a flow diagram illustrating another embodiment of a process 600 implemented by the patient monitor for measuring blood pressure of a wearer. FIG. 6 is similar in many respects to FIGS. 5A and 5B. For example, blocks 602-508 of FIG. 6 correspond to blocks 502-408 of FIG. 5A, respectively. Furthermore, blocks 614-520 correspond to blocks 554-460 of FIG. 5B, respectively.

As described above with reference to FIG. 5A and illustrated in blocks 602-508, the patient monitor 206 actuates a valve to initiate inflation, receives blood pressure data during inflation, filters the blood pressure data, and determines the blood pressure of the wearer. Upon determining the blood pressure of the wearer, the patient monitor assigns a confidence level to the blood pressure measurements, as illustrated in block 610. The confidence level assigned can be determined in any number of ways. For example, based on the amount and magnitude of the noise observed in the blood pressure data, the patient monitor can assign the confidence level. Alternatively, if an anomaly in the blood pressure data is detected or if the blood pressure data deviates beyond a threshold level a lower confidence level can be assigned to the blood pressure measurements. In an embodiment, prior measurements or other expectations or trend information may be used to determine confidence levels.

At determination block 612, the patient monitor 206 determines if the confidence level assigned to the inflationary blood pressure measurements are above a threshold confidence level. The threshold confidence level can be determined based on previous blood pressure measurements, historical information, clinical data from one or more wearers, or the like. If the confidence level assigned to the blood pressure measurements during inflation exceeds the threshold confidence level, the patient monitor 206 outputs the inflationary blood pressure measurements, as illustrated in block 628. The inflationary blood pressure measurements can be output to a display, a printer, another patient monitor, etc. Once output, the patient monitor 206 can actuate a valve to deflate the inflatable cuff 204 at a rate greater than would be used if the blood pressure measurements were taken during deflation. Alternatively, the patient monitor 206 can deflate the inflatable cuff 204 at the same rate as when blood pressure measurements taken during deflation.

If on the other hand, the confidence level assigned to the inflationary blood pressure measurements is less than the threshold confidence level, then the patient monitor can actuate the valve to initiate deflation of the inflatable cuff, as illustrated in block 614. As blocks 614-520 correspond to blocks 554-460 of FIG. 5B, additional details with respect to blocks 614-520 are provided above with reference to FIG. 5B.

Upon determining the blood pressure during deflation, the patient monitor 206 can assign a confidence level to the deflationary blood pressure measurements, as illustrated in block 622 and described in greater detail above with reference to block 610. Upon assigning the confidence level to the deflationary blood pressure measurements, the patient monitor 206 determines if the confidence level exceeds a threshold confidence, as illustrated in determination block 624, similar to the determination made in block 612. If the patient monitor 206 determines that the confidence level assigned to the deflationary blood pressure measurements does not exceed the confidence threshold, the patient monitor 206 can output an error, as illustrated in block 626. The error can indicate that neither the inflationary blood pressure measurements nor the deflationary blood pressure measurements exceeded the confidence threshold. In addition, the patient monitor 206 can recommend that additional blood pressure measurements be taken.

If on the other hand, the patient monitor determines that the confidence level assigned to the deflationary blood pressure measurements exceeds the confidence threshold, the patient monitor outputs the deflationary blood pressure measurements, as shown in block 628.

Fewer, more, or different blocks can be added to the process 600 without departing from the spirit and scope of the description. For example, in an embodiment, the patient monitor 206 automatically returns to step 602 upon outputting the error or determining that the confidence level did not exceed the confidence threshold, and repeats the process 600. In yet another embodiment, the patient monitor 206 outputs the error as well as the blood pressure measurements having the highest confidence level.

Figure 7:
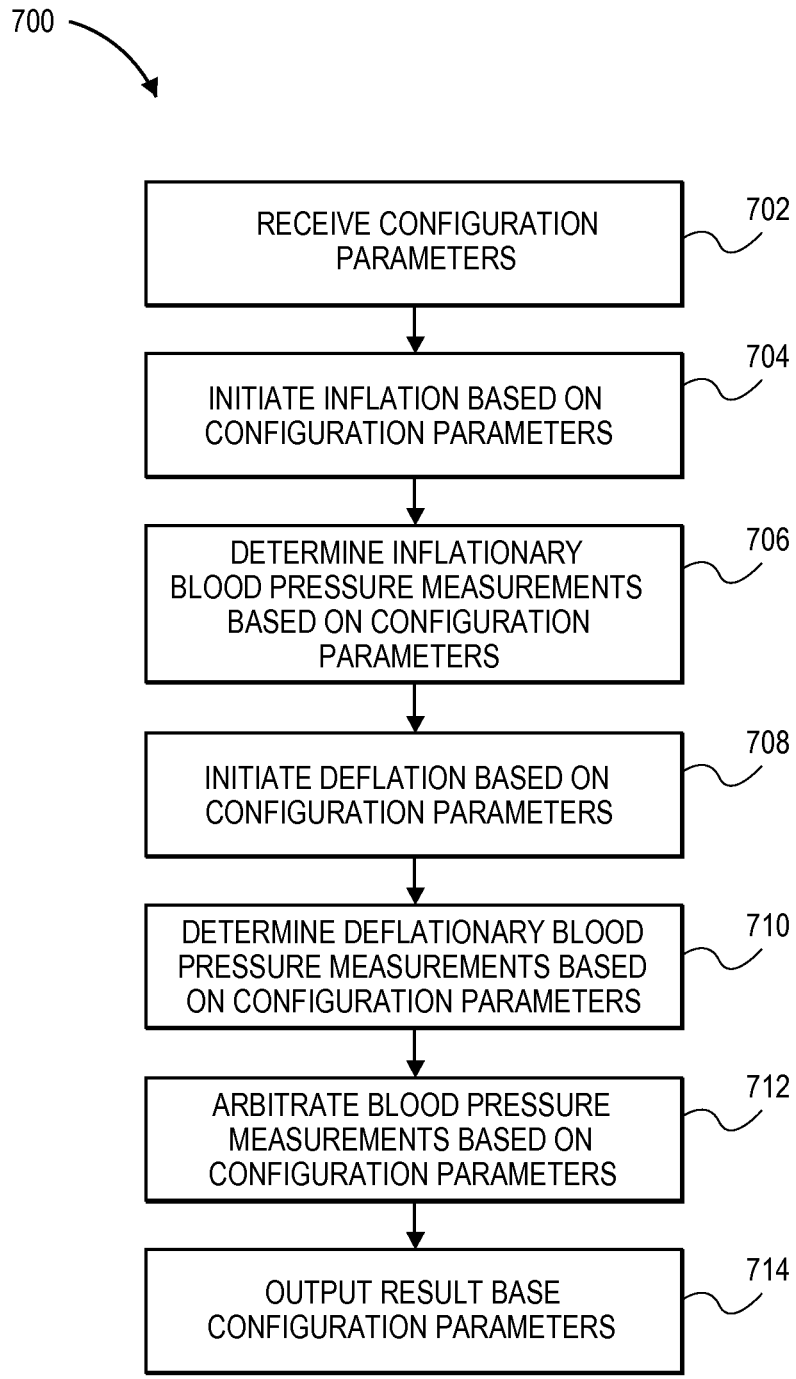
FIG. 7 is a flow diagram illustrating yet another embodiment of a process implemented by the patient monitor for measuring blood pressure of a wearer.

FIG. 7 is a flow diagram illustrating yet another embodiment of a process 700 implemented by the patient monitor 206 for measuring blood pressure of a wearer. At block 702, the patient monitor 206 receives configuration parameters. The configuration parameters can be set by a user, another patient monitor, or preset. The configuration parameters can include when to measure blood pressure, how to calculate the diastolic and systolic blood pressure, what measurements to display, confidence thresholds, etc. For example the configuration parameters can include whether to take blood pressure measurements during inflation, deflation, or both. In addition, the configuration parameters can include information regarding what process to use to determine the blood pressure measurements. For example, the patient monitor can determine the blood pressure measurements using the measured arterial pressure, the slopes of the pressure oscillations, maximum deflection points of the filtered blood pressure data, or other criteria. The configuration parameters can also include the confidence level to be used in determining whether the blood pressure measurements should be accepted. Furthermore, the configuration parameters can include what blood pressure measurements are to be output and how to determine which blood pressure measurements to output. For example, the configuration parameters can dictate that only blood pressure measurements having a confidence level greater than a threshold are to be output, or that the blood pressure measurements having the highest threshold are to be output. Additionally, the configuration parameters can dictate that both blood pressure measurements, average blood pressure measurements, and the like are to be output. Furthermore, the configuration parameters can include the frequency with which the blood pressure measurements are to be taken.

At block 704, the patient monitor initiates inflation based on the received configuration parameters. For example, the configuration parameters can dictate the rate at which the inflatable cuff 204 is to be inflated using the gas reservoir 202. In an embodiment, the inflatable cuff 204 is inflated at an approximately constant rate. In another embodiment, the inflatable cuff is not inflated at an approximately constant rate. In an embodiment, the inflatable cuff 204 is inflated in a relatively short amount of time or at a very high rate of inflation. In another embodiment, the inflatable cuff 204 is inflated more slowly.

At block 706 the inflationary blood pressure measurements are determined by the patient monitor 706 based on the configuration parameters. The configuration parameters can dictate whether and what method to use in determining the inflationary blood pressure measurements. Furthermore, the configuration parameters can dictate whether the blood pressure data is filtered and how. In an embodiment, the configuration parameters dictate that the inflationary blood pressure measurements are not to be taken based on the inflation rate. In another embodiment, the patient monitor determines the inflationary blood pressure measurements based on the slope and magnitude of the oscillations of the filtered blood pressure data during inflation based on the configuration parameters. In addition, the patient monitor can set confidence levels and perform other operations based on the configuration parameters.

Upon determining the inflationary blood pressure measurements, the patient monitor initiates deflation of the inflatable cuff 204 based on the configuration parameters. The configuration parameters can dictate the time and rate at which the inflatable cuff 204 deflates. For example, the configuration parameters can dictate a threshold pressure that when reached initiates the deflation. The threshold pressure can be based on personal information of the wearer or general safety levels. In an embodiment, the patient monitor initiates deflation based on a threshold pressure being reached for a predefined period of time based on the configuration parameters. In another embodiment, the patient monitor initiates deflation once the inflationary blood pressure measurements are taken.

Upon initiating deflation, the patient monitor determines deflationary blood pressure measurements based on one or more configuration parameters, as illustrated in block 710. As discussed previously, with reference to block 706 the configuration parameters can include any number of parameters that determine if and how the deflationary blood pressure measurements are taken, as well as if and how the blood pressure data is filtered. In addition, the patient monitor can set confidence levels and perform other operations based on the configuration parameters.

Upon determining the deflationary blood pressure measurements, the patient monitor arbitrates blood pressure measurements based on the configuration parameters. The patient monitor can arbitrate the blood pressure measurements based on any number of configuration parameters. For example, the patient monitor can arbitrate the blood pressure measurements based on the highest confidence level or whether a threshold confidence level was reached. Furthermore, the patient monitor can arbitrate based on expected values, previous values, averages or the like. Alternatively, the patient monitor can select both the inflationary and deflationary blood pressure measurements.

At block 714, the patient monitor outputs the results of the arbitration based on the configuration parameters. The output can include the inflationary blood pressure measurements, the deflationary blood pressure measurements, both or a combination of the two. The output can further include additional information, such as inflation rate, deflation rate, average blood pressure measurements depending on whether they were determined during inflation or deflation, etc.

Fewer, more, or different blocks can be added to the process 700 without departing from the spirit and scope of the description. For example, based on the blood pressure measurements, the configuration parameters can be changed and the process 700 can begin again.

Depending on the embodiment, certain acts, events, or functions of any of the methods described herein can be performed in a different sequence, can be added, merged, or left out all together (e.g., not all described acts or events are necessary for the practice of the method). Moreover, in certain embodiments, acts or events can be performed concurrently, e.g., through multi-threaded processing, interrupt processing, or multiple processors, rather than sequentially.

The various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment.

While the above detailed description has shown, described, and pointed out novel features as applied to various embodiments, it will be understood that various omissions, substitutions, and changes in the form and details of the device or process illustrated can be made without departing from the spirit of the disclosure. As will be recognized, certain embodiments of the inventions described herein can be embodied within a form that does not provide all of the features and benefits set forth herein, as some features can be used or practiced separately from others. The scope of the inventions is indicated by the appended claims rather than by the foregoing description. All changes which come within the meaning and range of equivalency of the claims are to be embraced within their scope.

What is claimed is:

1. A blood pressure monitoring system wearable by a monitored patient, the system comprising:
a housing;
an inflatable cuff configured to encompass a limb of a monitored patient;
a removable gas reservoir storing pressurized gas;
a chamber positioning the gas reservoir, wherein the housing is operably coupled with the chamber and the inflatable cuff to allow the blood pressure monitoring system to be worn on the limb of the monitored patient;
a gas pathway between the gas reservoir and the inflatable cuff;
at least one sensor outputting data signals responsive to pressure of the gas inside the inflatable cuff; and
a processing device configured to:
receive said signal from said at least one sensor,
determine a first blood pressure of the monitored patient prior to deflation of the inflatable cuff based at least on data signals received during inflation of the inflatable cuff;
assign a confidence level to the first blood pressure,
determine whether the confidence level satisfies a threshold confidence level, and
based at least upon a determination that the confidence level does not satisfy the threshold confidence level, determine a second blood pressure of the monitored patient based at least on data signals received during the deflation of the inflatable cuff.

2. The system of claim 1, wherein said processing device is further configured to cause a display to display at least one of the first blood pressure and the second blood pressure.

3. The system of claim 1, wherein said processing device comprises a personal computing device.

4. The system of claim 1, wherein said processing device comprises a phone executing one or more applications capable of said processing and said determining.

5. The system of claim 1, wherein said processing device controls the inflation and the deflation of the cuff through communication with one or more valves in said gas pathway.

6. The system of claim 1, wherein said processing device determines the first blood pressure during inflation.

7. The system of claim 6, wherein said processing device determines a systolic pressure as a magnitude oscillation of the signal and a diastolic pressure as a slope of the signal prior to the magnitude oscillation.

8. The system of claim 7, wherein the magnitude oscillation is the largest magnitude oscillation of the signal during inflation and the slope is the largest slope of the signal prior to the largest magnitude oscillation.

9. The system of claim 1, wherein said processing device determines the second blood pressure during deflation.

10. The system of claim 9, wherein said processing device determines a systolic pressure as a pressure of the inflatable cuff corresponding to a first slope of the signal prior to a magnitude oscillation and a diastolic pressure as a pressure of the inflatable cuff corresponding to a second slope of the signal following the magnitude oscillation.

11. The system of claim 10, wherein the magnitude oscillation is the largest magnitude oscillation of the signal during deflation, the first slope is the largest slope of the signal prior to the largest magnitude oscillation, and the second slope is the largest slope of the signal following the largest magnitude oscillation.

12. The system of claim 1, wherein said processing device implements a measurement protocol.

13. The system of claim 12, wherein the measurement protocol includes periodic measurements.

14. The system of claim 13, wherein the measurement protocol monitors other physiological parameters and initiates a blood pressure measurement when other physiological parameters exhibit a predetermined behavior.

15. The system of claim 14, wherein the other physiological parameters are responsive to oxygen saturation.

16. The system of claim 1, wherein said processing device communicates with electronics associated with the gas reservoir.

17. The system of claim 16, wherein the electronics associated with the gas reservoir indicate whether the gas reservoir is authorized.

18. The system of claim 16, wherein the electronics associated with the gas reservoir indicate gas reservoir usage.

19. The system of claim 18, wherein updated data responsive to usage is written to the electronics associated with the gas reservoir.

20. The system of claim 16, wherein the electronics associated with the gas reservoir indicate reservoir characteristics.

21. The system of claim 1, wherein said processing device is configured to display a waveform on a display device.

22. The system of claim 21, wherein the waveform is responsive to arterial pulse.

23. The system of claim 21, wherein the display device is multi-lingual.

24. The system of claim 21, wherein the display device includes a wellness indicator.

25. The system of claim 1, wherein the confidence level is based at least on a signal-to-noise ratio of the data signals received during inflation of the inflatable cuff.

26. The system of claim 1, wherein the confidence level is a first confidence level and said processing device is further configured to:
    assign a second confidence level to the second blood pressure; and
    cause a display to display at least one of the first blood pressure and the second blood pressure based at least on a comparison of the first confidence level and the second confidence level.

27. The system of claim 26, wherein the first confidence level is based at least on a signal-to-noise ratio of the data signals received during inflation of the inflatable cuff and the second confidence level is based at least on a signal-to-noise ratio of the data signals received during deflation of the inflatable cuff.

28. The system of claim 1, wherein the confidence level is based at least on a magnitude of noise in the data signals received during inflation of the inflatable cuff.

* * * * *